United States Patent [19]
Jones et al.

[11] Patent Number: 5,834,179
[45] Date of Patent: Nov. 10, 1998

[54] MORPHOGENIC PROTEIN COMPOSITIONS OF MATTER

[75] Inventors: William K. Jones, Brookline; Ronald F. Tucker, Holliston; David C. Rueger, Hopkinton; Hermann Oppermann, Medway; Engin Ozkaynak, Milford; Thangavel Kuberasampath, Medway, all of Mass.

[73] Assignee: Creative BioMolecules, Hopkinton, Mass.

[21] Appl. No.: 459,346

[22] Filed: Jun. 2, 1995

Related U.S. Application Data

[62] Division of Ser. No. 402,542, Mar. 13, 1995, which is a continuation of Ser. No. 40,510, Mar. 31, 1993, abandoned, which is a continuation-in-part of Ser. No. 29,335, Mar. 4, 1993, abandoned, and a continuation-in-part of Ser. No. 27,070, Mar. 4, 1993, abandoned, Ser. No. 971,091, Nov. 3, 1992, abandoned, Ser. No. 946,235, Sep. 16, 1992, abandoned, Ser. No. 938,336, Aug. 28, 1992, abandoned, and Ser. No. 923,780, Jul. 31, 1992, abandoned, which is a continuation-in-part of Ser. No. 752,857, Aug. 30, 1991, abandoned, and a continuation-in-part of Ser. No. 752,764, Aug. 30, 1991, abandoned, which is a continuation-in-part of Ser. No. 667,274, Mar. 11, 1991, abandoned.

[51] Int. Cl.$^6$ .............................. C12Q 1/00; G01N 33/53; G01N 33/542; G01N 33/537

[52] U.S. Cl. ................................. 435/4; 435/7.9; 435/7.1; 435/7.2; 435/7.92; 435/7.94; 435/7.95; 435/975; 436/503; 436/161; 436/518; 436/523; 436/524; 436/525; 436/526; 436/527; 436/528; 436/529; 436/530; 436/531; 436/536; 436/881; 436/815; 530/350

[58] Field of Search ..................................... 436/503, 518, 436/523–531, 536, 811, 815, 161; 530/350; 435/4, 7.1, 7.2, 7.9, 7.92, 7.94, 7.95, 975

[56] References Cited

U.S. PATENT DOCUMENTS

| | | |
|---|---|---|
| 4,294,753 | 10/1981 | Urist . |
| 4,455,256 | 6/1984 | Urist . |
| 4,857,456 | 8/1989 | Urist . |
| 5,106,748 | 4/1992 | Wozney et al. ........................ 435/252.3 |
| 5,393,739 | 2/1995 | Bentz et al. ............................... 514/12 |

OTHER PUBLICATIONS

Ngo et al, Protein Folding Problem & Tertiary Structure Prediction, Merz and LeGrand eds, pp. 491–495, 1994.

Bowie et al, Science vol. 247 p. 1306, Mar. 1990.

Celeste, et al., Identification of transforming growth factor β family members present in bone–inductive protein purified from bovine bone, PNAS, 87: 9843–9847 (1990).

Israel, et al., Expression and Characterization of Bone Morphogenetic Protein–2 in Chinese Hamster Ovary Cells, Growth Factors, 7: 139–150 (1992).

Lee, Expression of growth/differentiation factor 1 in the nervous system: Conservation of a bicistronic structure, PNAS, 88: 4250–4254 (1991).

Lyons, et al., Vgr–1, a mammalian gene related to Xenopus Vg–1, is a member of the transforming growth fact β gene superfamily, PNAS, 86: 4554–4558 (1989).

Ozkaynak, et al., OP–1 cDNA encodes an osteogenic protein in the TGF–β family, EMBO Journal, 9: 2085–2093 (1990).

Panganiban, et al., Biochemical Characterization of the Drosophila dpp Protein, a Member of the Transforming Growth Factor β Family of Growth Factors Molecular and Cellular Biology, 10: 2669–2677 (1990).

Urist, et al., Radioimmunoassay of Bone Morphogenetic Protein in Serum: A Tissue–Specific Parameter of Bone Metabolism, Proceedings of the Society for Experimental Biology & Medicine, 176: 472–475 (1984).

Wang, et al., Purification and characterization of other distinct bone–inducing factors, PNAS, 85: 9484–9488 (1988).

Wang, et al., Recombinant Human Bone Morphogenetic Protein Induces Bone Formation, PNAS, 87: 2220–2224 (1990).

Weeks, et al., A maternal mRNA Localized to the Vegetal Hemisphere in Xenopus Eggs Codes for a Growth Factor Cell, 51: 861–867 (1987).

Wharton, et al., Drosphila 60A gene, another transforming growth factor β family member, is closely related to human bone morphogenetic proteins, PNAS, 88: 9214–9218 (1991).

Wozney, et al., Novel Regulators of Bone Formation: Molecular Clones and Activities, Science, 242: 1528–1533 (1988).

*Primary Examiner*—Sheela Huff
*Attorney, Agent, or Firm*—Testa, Hurwitz & Thibeault, LLP

[57] ABSTRACT

Disclosed are novel compositions of morphogenic proteins constituting soluble forms of these proteins, antibodies that distinguish between soluble and mature forms, and method for producing these morphogenic proteins and antibodies.

7 Claims, 3 Drawing Sheets

```
OP-2:                    RAPR SQQPFVVTFFRASPSPIRTPRAVRPLRRRQPKKSNELPQANRLPGIFDDVHGSHGRQVC
OP-1:                                              RSIRSTGSKQRSQNRSKTPKNQEALRMANVAENSSSDQRQAC
Vgr-1:                                             RTTRSASSRRRQQSRNRSTQSDVSRGSGSSDYNGSELKTAC
BMP-5:                                             RSVRAANKRKNQNRNKSSSHQDSSRMSSVGDYNTSEQKQAC
60A:                                               RSKRSASHPRKRKKSVSPNNVPLLEPMESTRSC
DPP:                                               RSIRDVSGGEGGGKGGRNKRHARRPTRRKNHDDTC
BMP-2:             RHVRISRSLHQDEHSWSQIRPLLVTFGHDGKGHPLHK--REKRQAKH--KQRKRLKSSC
BMP-4:             RISRSLPQGSGNWAQLRPLLVTFGHDGRGHALTRRRAKRSPKHHSQRARKKNKNC
Vg-1:                                              RCKRPRKRSYSKLPFTASNIC
BMP-3: RKKRSTGVLLPLQ..................KSKNKKKQRKGPHRKSQTLQFDEQTLKKARRKQWIEPRNC
```

Fig. 2

MORPHOGENIC PROTEIN COMPOSITIONS OF MATTER

RELATED APPLICATIONS

This application is a divisional of (1) copending application U.S. Ser. No. 08/402,542 filed on Mar. 13, 1995, which is a continuation of U.S. Ser. No. 08/040,510, filed Mar. 31, 1993, now abandoned, which is a continuation-in-part of U.S. Ser. No. 08/029,335, Mar. 4, 1993, now abandoned; (2) U.S. Ser. No. 08/027,070, filed Mar. 4, 1993, now abandoned; (3) U.S. Ser. No. 07/971,091, filed Nov. 3, 1992, now abandoned; (4) U.S. Ser. No. 07/946,235, filed Sep. 16, 1992, now abandoned; (5) U.S. Ser. No. 07/938,336, Aug. 28, 1992, now abandoned; (6) U.S. Ser. No. 07/923,780, filed Jul. 31, 1992, now abandoned, which is a continuation-in-part of U.S. Ser. No. 07/752,857, filed Aug. 30, 1991, now abandoned; and (7) U.S. Ser. No. 07/752,764, filed Aug. 30, 1991, now abandoned, which is a continuation-in-part of U.S. Ser. No. 07/667,274, filed Mar. 11, 1991, now abandoned.

FIELD OF THE INVENTION

The present invention relates generally to morphogenic proteins and, more particularly, to compositions having improved solubility in aqueous solvents.

BACKGROUND OF THE INVENTION

Morphogenic proteins ("morphogens") are well known and described in the art. See, for example, U.S. Pat. Nos. 4,968,590; 5,011,691; 5,018,753; PCT US92/01968 and PCT US92/07432; as well as various articles published in the scientific literature, including Ozkaynak et al. (1992) *J. Biol. Chem.* 267:25220–25227 and Ozkaynak et al. (1991) *Biochem. Biophys. Res. Comm.* 179:116–123. The art has described how to isolate morphogenic proteins from bone, how to identify genes encoding these proteins and how to express them using recombinant DNA technology. The morphogenic proteins are capable of inducing endochondral bone formation and other tissue formation in a mammal when they are properly folded, dimerized and disulfide bonded to produce a dimeric species having the appropriate three dimensional conformation. The proteins have utility in therapeutic applications, either by direct or systemic administration. Where bone induction is desired, for example, the morphogen typically is provided to the desired site for bone formation in a mammal in association with a suitable matrix having the appropriate conformation to allow the infiltration, proliferation and differentiation of migrating progenitor cells. The morphogenic protein adsorbed to the surfaces of a suitable matrix is generally referred to in the art as an osteogenic device. The proteins can be isolated from bone or, preferably, the gene encoding the protein is produced recombinantly in a suitable host cell.

The morphogen precursor polypeptide chains share a common structural motif, including a N-terminal signal sequence and pro region, both of which are cleaved to produce a mature sequence, capable of disulfide bonding and comprising an N-terminal extension and a C-terminal domain whose amino acid sequence is highly conserved among members of the family. In their mature dimeric forms, the morphogens typically are fairly insoluble under physiological conditions. Increasing the solubility of these proteins has significant medical utility as it would enhance systemic administration of morphogens as therapeutics. Various carrier proteins, including serum albumin and casein are known to increase the solubility of morphogens (see, for example, PCT US92/07432). PCT US92/05309 (WO 93/00050) discusses the use of various solubilizing agents, including various amino acids and methyl esters thereof, as well as guanidine, sodium chloride and heparin, to increase the solubility of mature dimeric BMP2.

Improved methods for the recombinant expression of morphogenic proteins is an ongoing effort in the art. It is an object of this invention to provide an improvement in the methods for producing and purifying morphogenic proteins having high specific activity, and for formulating compositions and osteogenic devices comprising these proteins. Another object is to provide soluble forms of morphogenic proteins consisting essentially of amino acid sequences derived from morphogenic proteins. Another object is to provide formulations which stabilize the soluble complex of morphogenic proteins. Still another object is to provide means for distinguishing between soluble forms of the protein and the mature morphogenic species, to provide means for quantitating the amounts of these proteins in a fluid, including a body fluid, such as serum, cerebro-sprinal fluid or peritoneal fluid, and to provide polyclonal and monoclonal antibodies capable of distinguishing between these various species.

Another object is to provide antibodies and biological diagnostic assays for monitoring the concentration of morphogens and endogenous anti-morphogen antibodies present in a body fluid and to provide assays for detecting fluctuations in the concentrations of these proteins in a body fluid. U.S. Pat. No. 4,857,456 and Urist et al. (1984) *Proc. Soc. Exp. Biol. Med.* 176:472–475 describe a serum assay for detecting a protein purported to be a bone morphogenetic protein. The protein is not a member of the morphogen family of proteins described herein, differing in molecular weight, structural characteristics and solubility from these proteins.

SUMMARY OF THE INVENTION

It has now been discovered that morphogenic protein secreted into cultured medium from mammalian cells contains as a significant fraction of the secreted protein a soluble form of the protein, and that this soluble form comprises the mature dimeric species, including truncated forms thereof, noncovalently associated with at least one, and preferably two pro domains. It further has been discovered that antibodies can be used to discriminate between these two forms of the protein. These antibodies may be used as part of a purification scheme to selectively isolate the mature or the soluble form of morphogenic protein, as well as to quantitate the amount of mature and soluble forms produced. These antibodies also may be used as part of diagnostic treatments to monitor the concentration of morphogenic proteins in solution in a body and to detect fluctuations in the concentration of the proteins in their various forms. The antibodies and proteins also may be used in diagnostic assays to detect and monitor concentrations of endogenous anti-morphogen antibodies to the various forms of these proteins in the body.

An important embodiment of the invention is a dimeric protein comprising a pair of polypeptide subunits associated to define a dimeric structure having morphogenic activity. As defined herein and in parent, related applications, morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells.

Each of the subunits of the dimeric morphogenic protein comprises at least the 100 amino acid peptide sequence having the pattern of seven or more cysteine residues characteristic of the morphogen family. Preferably, at least one of the subunits comprises the mature form of a subunit of a member of the morphogen family, or an allelic, species, mutant or chimeric variant thereof, noncovalently complexed with a peptide comprising part or all of a pro region of a member of the morphogen family, or an allelic, species, chimeric or other sequence variant thereof. The pair of subunits and one or, preferably, two pro region peptides, together form a complex which is more soluble in aqueous solvents than the uncomplexed pair of subunits.

Preferably, both subunits comprise a mature form of a subunit of a member of the morphogen family or an allelic, species, chimeric or other sequence, variant thereof, and both subunits are noncovalently complexed with a pro region comprising peptide, or a fragment thereof. Most preferably, each subunit is the mature form of human OP-1, or a species, allelic or other mutant variant thereof, and the pro region is the entire or partial sequence of the pro region of human OP-1, or a species, allelic or other mutant variant thereof. Preferred pro regions are full length forms of the pro region. Pro region fragments preferably include the first 18 amino acids of the pro sequence. Other useful pro region fragments are truncated sequences of the intact pro region sequence, the truncation occurring at the proteolytic cleavage site Arg-Xaa-Xaa-Arg.

As used herein, the mature form of a morphogen protein subunit includes the intact C-terminal domain and intact or truncated forms of the N-terminal extensions. For example, useful mature forms of OP-1 include dimeric species defined by residues 293–431 of Seq ID No. 1, as well as truncated sequences thereof, including sequences defined by residues 300–431, 313–431, 315–431, 316–431 and 318–431. Note that this last sequence retains only about the last 10 residues of the N-terminal extension sequence. FIG. 2 presents the N-terminal extensions for a number of preferred morphogen sequences. Canonical Arg-Xaa-Xaa-Arg cleavage sites where truncation may occur are boxed or underlined in the figure. As will be appreciated by those skilled in the art, mature dimeric species may include subunit combinations having different N-terminal truncations.

Other soluble forms of morphogens include dimers of the uncleaved pro forms of these proteins (see below), as well as "hemi-dimers" wherein one subunit of the dimer is an uncleaved pro form of the protein, and the other subunit comprises the mature form of the protein, including truncated forms thereof, preferably noncovalently associated with a cleaved pro domain.

The soluble proteins of this invention are useful in the formation of therapeutic compositions for administration to a mammal, particularly a human, and for the development of biological assays for monitoring the concentration of these proteins and endogenous antibodies to these proteins in body fluids, including, but not limited to, serum, cerebrospinal fluid and peritoneal fluid.

The foregoing and other objects, features and advantages of the present invention will be made more apparent from the following detailed description of the invention.

BRIEF DESCRIPTION OF THE DRAWINGS

FIG. 2 lists the sequences of the N-terminal extensions of the mature forms of various morphogens.

DETAILED DESCRIPTION

Figure 1:
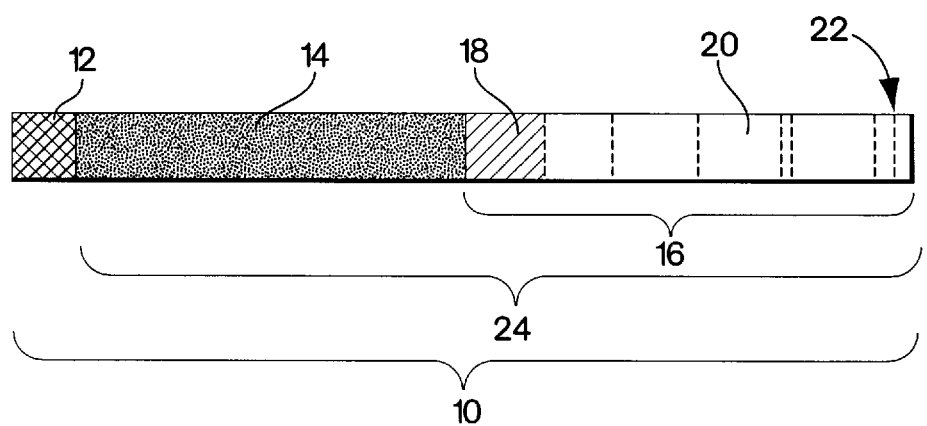
FIG. 1 is a schematic representation of a morphogen polypeptide chain as expressed from a nucleic acid encoding the sequence, wherein the cross-hatched region represents the signal sequence; the stippled region represents the pro domain; the hatched region represents the N-terminus ("N-terminal extension") of the mature protein sequence; and the open region represents the C-terminal region of the mature protein sequence defining the conserved seven cysteine domain, the conserved cysteines being indicated by vertical hatched lines.

A soluble form of morphogenic proteins now has been discovered wherein the proteins consist essentially of the amino acid sequence of the protein. The soluble form is a non-covalently associated complex comprising the pro domain or a fragment thereof, noncovalently associated or complexed with a dimeric protein species having morphogenic activity, each polypeptide of the dimer having less than 200 amino acids and comprising at least the C-terminal six, and preferably seven cysteine skeleton defined by residues 335–431 and 335–431, respectively, of Seq. ID No. 1. Preferably, the polypeptide chains of the dimeric species comprise the mature forms of these sequences, or truncated forms thereof. Preferred truncated forms comprise the intact C-terminal domain and at least 10 amino acids of the N-terminal extension sequence. The soluble forms of these morphogenic proteins may be isolated from cultured cell medium, a mammalian body fluid, or may be formulated in vitro.

In vivo, under physiological conditions, the pro domain may serve to enhance the transportability of the proteins, and/or to protect the proteins from proteases and scavenger molecules, including antibodies. The pro domains also may aid in targeting the proteins to a particular tissue and/or to present the morphogen to a morphogen cell surface receptor by interaction with a co-receptor molecule. The isolated proteins may be used in therapeutic formulations, particularly for oral or parenteral administration, and in the development of diagnostic assays to monitor the level of endogenous morphogens and endogenous anti-morphogen antibodies.

Detailed descriptions of the utility of these morphogens in therapies to regenerate lost or damaged tissues and/or to inhibit the tissue destructive effects of tissue disorders or diseases, are provided in co-pending U.S. patent application Ser. Nos. 07/752,764, filed Aug. 31, 1991; 07/938,336, filed Aug. 28, 1998; 07/923,780, filed Jul. 31, 1992; 07/945,292, filed Sep. 15, 1992; 07/945,285, filed Sep. 15, 1992; 07/938,337, filed Aug. 28, 1992; 07/922,813, filed Jul. 31, 1992; 07/946,235, filed Sep. 16, 1992; 07/946,238, filed Sep. 16, 1992; 07/945,286, filed Sep. 15, 1992; and 07/971,071, filed Nov. 11, 1992, the disclosures of which are incorporated herein by reference. Morphogens, including the soluble morphogen complexes of this invention, are envisioned to have particular utility as part of therapies for regenerating lost or damaged bone, dentin, periodontal, liver, cardiac, lung and nerve tissue, as well as for protecting these tissues from the tissue destructive effects associated with an immunological response. The proteins also are anticipated to provide a tissue protective effect in the treatment of metabolic bone disorders, such as osteoporosis, osteomalacia and osteosarcoma; in the treatment of liver disorders, including cirrhosis, hepatitis, alcohol liver disease and hepatic encephalopathy; and in the treatment or prevention of ischemia reperfusion-associated tissue damage, particularly to nerve or cardiac tissue.

Presented below are detailed descriptions of useful soluble morphogen complexes of this invention, as well as how to make and use them.

I. Useful Soluble Morphogen Complexes-Protein Considerations

Among the morphogens useful in this invention are proteins originally identified as osteogenic proteins, such as the OP-1, OP-2 and CBMP2 proteins, as well as amino acid sequence-related proteins such as DPP (from Drosophila), Vg1 (from Xenopus), Vgr-1 (from mouse, see U.S. Pat. No. 5,011,691 to Oppermann et al.), GDF-1 (from mouse, see Lee (1991) PNAS 88:4250–4254), 60A protein (from Drosophila, see Wharton et al. (1991) PNAS 88:9214–9218), and the recently identified OP-3.

The members of this family, which are a subclass of the TGF-β super-family of proteins, share characteristic structural features, represented schematically in FIG. 1, as well as substantial amino acid sequence homology in their C-terminal domains, including a conserved seven cysteine structure. As illustrated in the figure, the proteins are translated as a precursor polypeptide sequence 10, having an N-terminal signal peptide sequence 12, (the "pre pro" region, indicated in the figure by cross-hatching), typically less than about 30 residues, followed by a "pro" region 14, indicated in the figure by stippling, and which is cleaved to yield the mature sequence 16. The mature sequence comprises both the conserved C-terminal seven cysteine domain 20, and an N-terminal sequence 18, referred to herein as an N-terminal extension, and which varies significantly in sequence between the various morphogens. Cysteines are represented in the figure by vertical hatched lines 22. The polypeptide chains dimerize and these dimers typically are stabilized by at least one interchain disulfide bond linking the two polypeptide chain subunits.

The signal peptide is cleaved rapidly upon translation, at a cleavage site that can be predicted in a given sequence using the method of Von Heijne ((1986) *Nucleic Acids Research* 14:4683–4691.) The "pro" form of the protein subunit, 24, in FIG. 1, includes both the pro domain and the mature domain, peptide bonded together. Typically, this pro form is cleaved while the protein is still within the cell, and the pro domain remains noncovalently associated with the mature form of the subunit to form a soluble species that appears to be the primary form secreted from cultured mammalian cells. Typically, previous purification techniques utilized denaturing conditions that disassociated the complex.

Other soluble forms of morphogens secreted from mammalian cells include dimers of the pro forms of these proteins, wherein the pro region is not cleaved from the mature domain, and "hemi-dimers", wherein one subunit comprises a pro form of the polypeptide chain subunit and the other subunit comprises the cleaved mature form of the polypeptide chain subunit (including truncated forms thereof), preferably noncovalently associated with a cleaved pro domain.

The isolated pro domain typically has a substantial hydrophobic character, as determined both by analysis of the sequence and by characterization of its properties in solution. The isolated pro regions alone typically are not significantly soluble in aqueous solutions, and require the presence of denaturants, e.g., detergents, urea, guanidine HCl, and the like, and/or one or more carrier proteins. Accordingly, without being limited to any given theory, the non-covalent association of the cleaved pro region with the mature morphogen dimeric species likely involves interaction of a hydrophobic portion of the pro region with a corresponding hydrophobic region on the dimeric species, the interaction of which effectively protects or "hides" an otherwise exposed hydrophobic region of the mature dimer from exposure to aqueous environments, enhancing the affinity of the mature dimer species for aqueous solutions.

Morphogens comprise a subfamily of proteins within the TGF-β superfamily of structurally related proteins. Like the morphogens described herein, TGF-β also has a pro region which associates non-covalently with the mature TGF-β protein form. However, unlike the morphogens, the TGF-β pro region contains numerous cysteines and forms disulfide bonds with a specific binding protein. The TGF-β pro domain also is phosphorylated at one or more mannose residues, while the morphogen pro regions typically are not.

Useful pro domains include the full length pro regions described below, as well as various truncated forms hereof, particularly truncated forms cleaved at proteolytic Arg-Xaa-Xaa-Arg cleavage sites. For example, in OP-1, possible pro sequences include sequences defined by residues 30–292 (full length form); 48–292; and 158–292. Soluble OP-1 complex stability is enhanced when the pro region comprises the full length form rather than a truncated form, such as the 48–292 truncated form, in that residues 30–47 show sequence homology to the N-terminal portions of other morphogens, and are believed to have particular utility in enhancing complex stability for all morphogens. Accordingly, currently preferred pro sequences are those encoding the full length form of the pro region for a given morphogen (see below). Other pro sequences contemplated to have utility include biosynthetic pro sequences, particularly those that incorporate a sequence derived from the N-terminal portion of one or more morphogen pro sequences.

Table I, below, describes the various preferred morphogens identified to date, including their nomenclature as used herein, the sequences defining the various regions of the subunit sequences, their Seq. ID references, and publication sources for their nucleic acid and amino acid sequences. The disclosure of these publications is incorporated herein by reference. The mature protein sequences defined are the longest anticipated forms of these sequences. As described above, shorter, truncated forms of these sequences also are contemplated. Preferably, truncated mature sequences include at least 10 amino acids of the N-terminal extension. FIG. 2 lists the N-terminal extensions for a number of the preferred morphogen sequences described below. Arg-Xaa-xaa-Arg cleavage sites that may yield truncated sequences of the mature subunit form are boxed or underlined in the figure.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1"), or mouse OP-1 ("mOP-1".) The cDNA sequences and the amino acids encoding the full length proteins are provided in Seq. Id Nos. 1 and 2 (hOP1) and Seq. ID Nos. 3 and 4 (mOP1.) The mature proteins are defined by residues 293–431 (hOP1) and 292–430 (mOP1), wherein |

TABLE I-continued

| | |
|---|---|
| | the conserved seven cysteine skeleton is defined by residues 330–431 and 329–430, respectively, and the N-terminal extensions are defined by residues 293–329 and 292–329, respectively. The "pro" regions of the proteins, cleaved to yield the mature, morphogenically active proteins, are defined essentially by residues 30–292 (hOP1) and residues 30–291 (mOP1). |
| "OP-2" | refers generically to the group of active proteins expressed from part or all of a DNA sequence encoding OP-2 protein, including allelic and species variants thereof, e.g., human OP-2 ("hOP-2") or mouse OP-2 ("mOP-2".) The full length proteins are provided in Seq. ID Nos. 5 and 6 (hOP2) and Seq. ID Nos. 7 and 8 (mOP2.) The mature proteins are defined essentially by residues 264–402 (hOP2) and 261–399 (mOP2), wherein the conserved seven cysteine skeleton is defined by residues 301–402 and 298–399, respectively, and the N-terminal extensions are defined by residues 264–300 and 261–297, respectively. The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for both OP-2 proteins.) |
| "OP-3" | refers generically to the group of active proteins expressed from part or all of a DNA sequence encoding OP-3 protein, including allelic and species variants thereof, e.g., mouse OP-3 ("mOP-3".) The full length protein is provided in Seq. ID No. 9. The mature protein is defined essentially by residues 261–399 or 264–399, wherein the conserved seven cysteine skeleton is defined by residues 298–399 and the N-terminal extension is defined by residues 264–297 or 261–297. The "pro" region of the protein, cleaved to yield the mature, morphogenically active proteins likely is defined essentially by residues 20–262. |
| "BMP2/BMP4" | refers to protein sequences encoded by the human BMP2 and BMP4 genes. The amino acid sequence for the full length proteins, referred to in the literature as BMP2A and BMP2B, or BMP2 and BMP4, appear in Seq. ID Nos. 10 and 11, respectively, and in Wozney, et al. (1988) Science 242: 1528–1534. The pro domain for BMP2 (BMP2A) likely includes residues 25–248 or 25–282; the mature protein, residues 249–396 or 283–396, of which residues 249–296/283–296 define the N-terminal extension and 295–396 define the C-terminal domain. The pro domain for BMP4 (BMP2B) likely includes residues 25–256 or 25–292; the mature protein, residues 257–408 or 293–408, of which 257–307/293–307 define the N-terminal extension, and 308–408 define the C-terminal domain. |
| "DPP" | refers to protein sequences encoded by the Drosophila DPP gene. The amino acid sequence for the full length protein, including the mature form and the pro region, appears in Seq. ID No. 12 and in Padgett, et al (1987) Nature 325: 81–84. The pro domain likely extends from the signal peptide cleavage site to residue 456; the mature protein likely is defined by residues 457–588, where residues 457–586 define the N-terminal extension and 487–588 define the C-terminal domain. |
| "Vg1" | refers to protein sequences encoded by the Xenopus Vg1 gene. The amino acid sequence for the full length protein, including the mature form and the pro region, appears in Seq. ID No. 13 and in Weeks (1987) Cell 51: 861–867. The pro domain likely extends from the signal peptide cleavage site to residue 246; the mature protein likely is defined by residues 247–360, where residues 247–258 define the N-terminal extension, and residues 259–360 define the C-terminal domain. |
| "Vgr-1" | refers to protein sequences encoded by the murine Vgr-1 gene. The amino acid sequence for the full length protein, including the mature form and the pro region, appears in Seq. ID No. 14 and in Lyons, et al, (1989) PNAS 86: 4554–4558. The pro domain likely extends from the signal peptide cleavage site to residue 299; the mature protein likely is defined by residues 300–438, where residues 300–336 define the N-terminal extension and residues 337–438 define the C-terminus. |
| "GDF-1" | refers to protein sequences encoded by the human GDF-1 gene. The cDNA and encoded amino sequence for the full length protein is provided in Seq. ID. No. 15 and Lee (1991) PNAS 88: 4250–4254. The pro domain likely extends from the signal peptide cleavage site to residue 214; the mature protein likely is defined by residues 215–372, where residues 215–256 define the N-terminal extension and residues 257–372 define the C-terminus. |
| "60A" | refers to protein sequences encoded by the Drosophila 60A gene. The amino acid sequence for the full length protein appears in Seq. ID No. 16 and in Wharton et al. (1991) PNAS 88: 9214–9218) The pro domain likely extends from the signal peptide cleavage site to residue 324; the mature protein likely is defined by residues 325–455, wherein residues 325–353 define the N-terminal extension and residues 354–455 define the C-terminus. |
| "BMP3" | refers to protein sequences encoded by the human BMP3 gene. The amino acid sequence for the full length protein, including the mature form and the pro region, appears in Seq. ID No. 17 and in Wozney et al. (1988) Science 242: 1528–1534. The pro domain likely extends from the signal peptide cleavage site to residue 290; the mature protein likely is defined by residues 291–472, wherein residues 291–370 define the N-terminal extension and residues 371–472 define the C-terminus. |
| "BMP5" | refers to protein sequences encoded by the human BMP5 gene. The amino acid sequence for the full length protein, including the mature form and the pro region, appears in Seq. ID No. 18 and in Celeste, et al. (1990) PNAS 87: 9843–9847. The pro domain likely extends from the signal peptide cleavage site to residue 316; the mature protein likely is defined by residues 317–454, where residues 317–352 define the N-terminus and residues 352–454 define the C-terminus. |
| "BMP6" | refers to protein sequences encoded by the human BMP6 gene. The amino acid sequence for the full length protein, including the mature form and the pro region, appears in Seq. ID No. 16 and in Celeste, et al. (1990) PNAS 87: 9843–5847. The pro domain likely includes extends from the signal peptide cleavage site to residue 374; the mature sequence likely includes residues 375–513, where residues 375–411 define the N-terminus and residues 412–513 define the C-terminus. |

Note that the OP-2 and OP-3 proteins have an additional cysteine residue in the C-terminal region (e.g., see residue 341 in SEQ. ID. NO. 5), in addition to the conserved cysteine skeleton in common with the other proteins in this family. The GDF-1 protein has a four amino acid insert within the conserved skeleton ("Gly-Gly-Pro-Pro") but this insert likely does not interfere with the relationship of the cysteines in the folded structure. In addition, the CBMP2 proteins are missing one amino acid residue within the cysteine skeleton.

The dimeric morphogen species are inactive when reduced, but are active as oxidized homodimers and when oxidized in combination with other morphogens of this invention. Thus, as defined herein, a morphogen useful in a soluble morphogen complex is a dimeric protein comprising a pair of polypeptide chains, wherein each polypeptide chain has less than 200 amino acids and comprises at least the C-terminal six, preferably seven cysteine skeleton defined by residues 335–431 of Seq. ID No. 1, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. The solubility of these structures is improved when the mature dimeric form of a morphogen, in accordance with the invention, is complexed with at least one, and preferably two, pro domains.

Various generic sequences (Generic Sequence 1–6) defining preferred C-terminal sequences useful in the soluble morphogens of this invention are described in U.S. Ser. No. 07/923,780, incorporated herein above by reference. Two currently preferred generic sequences are described below.

Generic Sequence 7 (Seq. ID No. 20) and Generic Sequence 8 (Seq. ID No. 21) disclosed below, accommodate the homologies shared among preferred morphogen protein family members identified to date, including OP-1, OP-2, OP-3, CBMP2A, CBMP2B, BMP3, 60A, DPP, Vg1, BMP5, BMP6, Vrg-1, and GDF-1. The amino acid sequences for these proteins are described herein (see Sequence Listing) and/or in the art, as well as in PCT publication U.S. 92/07358, filed Aug. 28, 1992, for example. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences allow for an additional cysteine at position 41 (Generic Sequence 7) or position 46 (Generic Sequence 8), providing an appropriate cysteine skeleton where inter- or intramolecular disulfide bonds can form, and containing certain critical amino acids which influence the tertiary structure of the proteins.

Generic Sequence 7

Leu Xaa Xaa Xaa Phe
1               5

Xaa Xaa Xaa Gly Trp Xaa Xaa Xaa Xaa
              10

Xaa Xaa Pro Xaa Xaa Xaa Xaa Ala
15                  20

Xaa Tyr Cys Xaa Gly Xaa Cys Xaa
        25              30

Xaa Pro Xaa Xaa Xaa Xaa
            35

Xaa Xaa Xaa Asn His Ala Xaa Xaa
        40                  45

Xaa Xaa Xaa Xaa Xaa Xaa Xaa
            50

Xaa Xaa Xaa Xaa Xaa Xaa Cys
55                      60

Cys Xaa Pro Xaa Xaa Xaa Xaa Xaa
            65

Xaa Xaa Xaa Leu Xaa Xaa Xaa
70                  75

Xaa Xaa Xaa Xaa Val Xaa Leu Xaa
            80

Xaa Xaa Xaa Xaa Met Xaa Val Xaa
85                  90

Xaa Cys Xaa Cys Xaa
        95 wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res. 13=(Trp or Ser); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28=(Glu, Lys, Asp, Gln or Ala); Xaa at res.30= (Ala, Ser, Pro, Gln, Ile or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40= (Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53= (Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86= (Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala) and Xaa at res.97=(His or Arg).

As described above, Generic Sequence 8 (Seq. ID No. 21) includes all of Generic Sequence 7 and in addition includes the following sequence at its N-terminus:

Cys Xaa Xaa Xaa Xaa
 1               5

Accordingly, beginning with residue 7, each "Xaa" in Generic Seq. 8 is a specified amino acid defined as for Generic Seq. 7, with the distinction that each residue number described for Generic Sequence 7 is shifted by five in Generic Seq. 8. Thus, "Xaa at res.2 CRP-081CP =(Tyr or Lys)" in Gen. Seq. 7 refers to Xaa at res. 7 in Generic Seq. 8. In Generic Seq. 8, Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr).

Accordingly, other useful sequences defining preferred C-terminal sequences are those sharing at least 70% amino acid sequence homology or "similarity", and preferably 80% homology or similarity with any of the sequences incorporated into Generic Seq. 7 and 8 above. These are anticipated to include allelic, species and mutant variants, as well as novel members of this morphogenic family of proteins. As used herein, "amino acid sequence homology" is understood to mean amino acid sequence similarity, and homologous sequences share identical or similar amino acids, where similar amino acids are conserved amino acids as defined by Dayoff et al., *Atlas of Protein Sequence and Structure*; vol.5, Suppl.3, pp.345–362 (M. O. Dayoff, ed., Nat'l BioMed. Research Fdn., Washington D.C. 1978.) Thus, a candidate sequence sharing 70% amino acid homology with a reference sequence requires that, following alignment of the candidate sequence with the reference sequence, 70% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all homologies and identities calculated use OP-1 as the reference sequence. Also as used herein, sequences are aligned for homology and identity calculations using the method of Needleman et al. (1970) *J.Mol. Biol.* 48:443–453 and identities calculated by the Align program (DNAstar, Inc.) In all cases, internal gaps and amino acid insertions in the candidate sequence as aligned are ignored when making the homology/identity calculation.

Also as used herein, sequence variant is understood to mean an amino acid variant form of the morphogen protein, wherein the amino acid change or changes in the sequence do not alter significantly the morphogenic activity (e.g., tissue regeneration activity) of the protein, and the variant molecule performs substantially the same function in substantially the same way as the naturally occurring form of the molecule. Sequence variants may include single or multiple amino acid changes, and are intended to include chimeric sequences as described below. The variants may be naturally occurring or may be biosynthetically induced by using standard recombinant DNA techniques or chemical protein synthesis methodologies.

The currently most preferred protein sequences useful in soluble morphogen complexes in this invention include those having greater than 60% identity, preferably greater than 65% identity, with the amino acid sequence defining the conserved six cysteine skeleton of hOP1 (e.g., residues 335–431 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 22).

Useful N-terminal extension sequences are listed in FIG. 2 for use with the C-terminal domains described above. Also as described above, the full length N-terminal extensions, or truncated forms thereof, may be used in preferred dimeric species. The mature dimeric species may be produced from intact DNAs, or truncated forms thereof. It also is envisioned as an embodiment of the invention that chimeric morphogen sequences can be used. Thus, DNAs encoding chimeric morphogens may be constructed using part or all of N-terminal extension from one morphogen and a C-terminal domain derived from one or more other morphogens. These chimeric proteins may be synthesized using standard recombinant DNA methodology and/or automated chemical nucleic acid synthesis methodology well described in the art.

Other chimeric morphogens include soluble morphogen complexes where the pro domain is encoded from a DNA sequence corresponding to one morphogen, and part or all of the mature domain is encoded by DNA derived from other, different morphogen(s). These soluble chimerics may be produced from a single synthetic DNA as described below, or, alternatively, may be formulated in vitro from isolated components also as described herein below.

Finally, the morphogen pro domains and/or mature form N-terminal extensions themselves may be useful as tissue targeting sequences. As described above, the morphogen family members share significant sequence homology in their C-terminal active domains. By contrast, the sequences diverge significantly in the sequences which define the pro domain and the N-terminal 39 amino acids of the mature protein. Accordingly, the pro domain and/or N-terminal extension sequence may be morphogen-specific. Accordingly, part or all of these morphogen-specific sequences may serve as tissue targeting sequences for the morphogens described herein. For example, the N-terminal extension and/or pro domains may interact specifically with one or more molecules at the target tissue to direct the morphogen associated with the pro domain to that tissue. Thus, for example, the morphogen-specific sequences of OP-1, BMP2 or BMP4, all of which proteins are found naturally associated with bone tissue (see, for example, U.S. Pat. No. 5,011,691) may be particularly useful sequences when the morphogen complex is to be targeted to bone. Similarly, BMP6 (or Vgr-1) specific sequences may be used when targeting to lung tissue is desired. Alternatively, the morphogen-specific sequences of GDF-1 may be used to target soluble morphogen complexes to nerve tissue, particularly brain tissue, where GDF-1 appears to be primarily expressed (see, for example, U.S. Ser. No. 922,813 and Lee, PNAS, 88:4250–4254 (1991), incorporated herein by reference).

II. Recombinant Production of Soluble Morphogen Complexes

Soluble morphogen complexes can be produced from eukaryotic host cells, preferably mammalian cells, using standard recombinant expression techniques. An exemplary protocol currently preferred, is provided below, using a particular vector construct and chinese hamster ovary (CHO) cell line. Those skilled in the art will appreciate that other expression systems are contemplated to be useful, including other vectors and other cell systems, and the invention is not intended to be limited to soluble morphogenic protein complexes produced only by the method detailed hereinbelow. Similar results to those described herein have been observed using recombinant expression systems developed for COS and BSC cells.

Morphogen DNA encoding the precursor sequence is subcloned into an insertion site of a suitable, commercially available pUC-type vector (e.g., pUC-19, ATCC #37254, Rockville, Md.), along with a suitable promoter/enhancer sequences and 3' termination sequences. Useful DNA sequences include the published sequences encoding these proteins, and/or synthetic constructs. Currently preferred promoter/enhancer sequences are the CMV promoter (human cytomegalovirus major intermediate—early promoter) and the mouse mammary tumor virus promoter (mMTV) boosted by the rous sarcoma virus LTR enhancer sequence (e.g., from Clontech, Inc., Palo Alto). Expression also may be further enhanced using transactivating enhancer sequences. The plasmid also contains DHFR as an amplifiable marker, under SV40 early promoter control (ATCC #37148). Transfection, cell culturing, gene amplification and protein expression conditions are standard conditions, well known in the art, such as are described, for example in Ausubel et al., ed., Current Protocols in Molecular Biology, John Wiley & Sons, N.Y. (1989). Briefly, transfected cells are cultured in medium containing 0.1–0.5% dialyzed fetal calf serum (FCS) and stably transfected high expression cell lines are obtained by subcloning and evaluated by standard Western or Northern blot. Southern blots also are used to assess the state of integrated sequences and the extent of their copy number amplification.

A currently preferred expression vector contains the DHFR gene, under SV40 early promoter control, as both a selection marker and as an inducible gene amplifier. The DNA sequence for DHFR is well characterized in the art, and is available commercially. For example, a suitable vector may be generated from pMAM-neo (Clontech, Inc., Palo Alto, Calif.) by replacing the neo gene (BamHI digest) with an SphI-BamHI, or a PvuII-BamHI fragment from pSV5-DHFR (ATCC #37148), which contains the DHFR gene under SV40 early promoter control. A BamHI site can be engineered at the SphI or PvuII site using standard techniques (e.g., by linker insertion or site-directed mutagenesis) to allow insertion of the fragment into the vector backbone. The morphogen DNA can be inserted into the polylinker site downstream of the MMTV-LTR sequence (mouse mammary tumor virus LTR). The CMV promoter sequence then may be inserted into the expression vector (e.g., from pCDM8, Invitrogen, Inc.) The SV40 early promoter, which drives DHFR expression, preferably is modified in these vectors to reduce the level of DHFR mRNA produced.

The currently preferred mammalian cell line is a CHO Chinese hamster ovary, cell line, and the preferred procedure for establishing a stable morphogen production cell line with high expression levels comprises transfecting a stable CHO cell line, preferably CHO-DXB11, with the expression vector described above, isolating clones with high morphogen expression levels, and subjecting these clones to cycles of subcloning using a limited dilution method described below to obtain a population of high expression clones. Subcloning preferably is performed in the absence of MTX to identify stable high expression clones which do not require addition of MTX to the growth media for morphogen production.

In the subcloning protocol cells are seeded on ten 100 mm petri dishes at a cell density of either 50 or 100 cells per plate, with or preferably without MTX in the culture media. After 14 days of growth, clones are isolated using cloning cylinders and standard procedures, and cultured in 24-well plates. Clones then are screened for morphogen expression by Western immunoblots using standard procedures, and morphogen expression levels compared to parental lines. Cell line stability of high expression subclones then is determined by monitoring morphogen expression levels over multiple cell passages (e.g., four or five passages).

III. Isolation of Soluble morphogen complex from conditioned media or body fluid Morphogens are expressed from mammalian cells as soluble complexes. Typically, however the complex is disassociated during purification, generally by exposure to denaturants often added to the purification solutions, such as detergents, alcohols, organic solvents, chaotropic agents and compounds added to reduce the pH of the solution. Provided below is a currently preferred protocol for purifying the soluble proteins from conditioned media (or, optionally, a body fluid such as serum, cerebro-spinal or peritoneal fluid), under non-denaturing conditions. The method is rapid, reproducible and yields isolated soluble morphogen complexes in substantially pure form.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. The present protocol has general applicability to the purification of a variety of morphogens, all of which are anticipated to be isolatable using only minor modifications of the protocol described below. An alternative protocol also envisioned to have utility an immunoaffinity column, created using standard procedures and, for example, using antibody specific for a given morphogen pro domain (complexed, for example, to a protein A-conjugated Sepharose column.) Protocols for developing immunoaffinity columns are well described in the art, (see, for example, *Guide to Protein Purification*, M. Deutscher, ed., Academic Press, San Diego, 1990, particularly sections VII and XI.)

In this experiment OP-1 was expressed in CHO cells as described above. The CHO cell conditioned media containing 0.5% FBS was initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC step separates the soluble OP-1 from the bulk of the contaminating serum proteins that elute in the flow through and 35 mM imidazole wash fractions. The Zn-IMAC purified soluble OP-1 is next applied to an S-Sepharose cation-exchange column equilibrated in 20 mM $NaPO_4$ (pH 7.0) with 50 mM NaCl. This S-Sepharose step serves to further purify and concentrate the soluble OP-1 complex in preparation for the following gel filtration step. The protein was applied to a Sephacryl S-200HR column equilibrated in TBS. Using substantially the same protocol, soluble morphogens also may be isolated from one or more body fluids, including serum, cerebro-spinal fluid or peritoneal fluid.

IMAC was performed using Chelating-Sepharose (Pharmacia) that had been charged with three column volumes of 0.2 M $ZnSO_4$. The conditioned media was titrated to pH 7.0 and applied directly to the ZN-IMAC resin equilibrated in 20 mM HEPES (pH 7.0) with 500 mM NaCl. The Zn-IMAC resin was loaded with 80 mL of starting conditioned media per mL of resin. After loading the column was washed with equilibration buffer and most of the contaminating proteins were eluted with 35 mM imidazole (pH 7.0) in equilibration buffer. The soluble OP-1 complex is then eluted with 50 mM imidazole (pH 8.0) in 20 mM HEPES and 500 mM NaCl.

The 50 mM imidazole eluate containing the soluble OP-1 complex was diluted with nine volumes of 20 mM $NaPO_4$ (pH 7.0) and applied to an S-Sepharose (Pharmacia) column equilibrated in 20 mM $NaPO_4$ (pH 7.0) with 50 mM NaCl. The S-Sepharose resin was loaded with an equivalent of 800 mL of starting conditioned media per mL of resin. After loading the S-Sepharose column was washed with equilibration buffer and eluted with 100 mM NaCl followed by 300 mM and 500 mM NaCl in 20 mM $NaPO_4$ (pH 7.0). The 300 mM NaCl pool was further purified using gel filtration chromatography. Fifty mls of the 300 mm NaCl eluate was applied to a 5.0×90 cm Sephacryl S-200HR (Pharmacia) equilibrated in Tris buffered saline (TBS), 50 mM Tris, 150 mM NaCl (pH 7.4). The column was eluted at a flow rate of 5 mL/minute collecting 10 mL fractions. The apparent molecular of the soluble OP-1 was determined by comparison to protein molecular weight standards (alcohol dehydrogenase (ADH, 150 kDa), bovine serum albumin (BSA, 68 kDa), carbonic anhydrase (CA, 30 kDa) and cytochrome C (cyt C, 12.5 kDa). (see FIG. 3) The purity of the S-200 column fractions was determined by separation on standard 15% polyacrylamide SDS gels stained with coomassie blue. The identity of the mature OP-1 and the pro-domain was determined by N-terminal sequence analysis after separation of the mature OP-1 from the pro-domain using standard reverse phase C18 HPLC.

Figure 3:
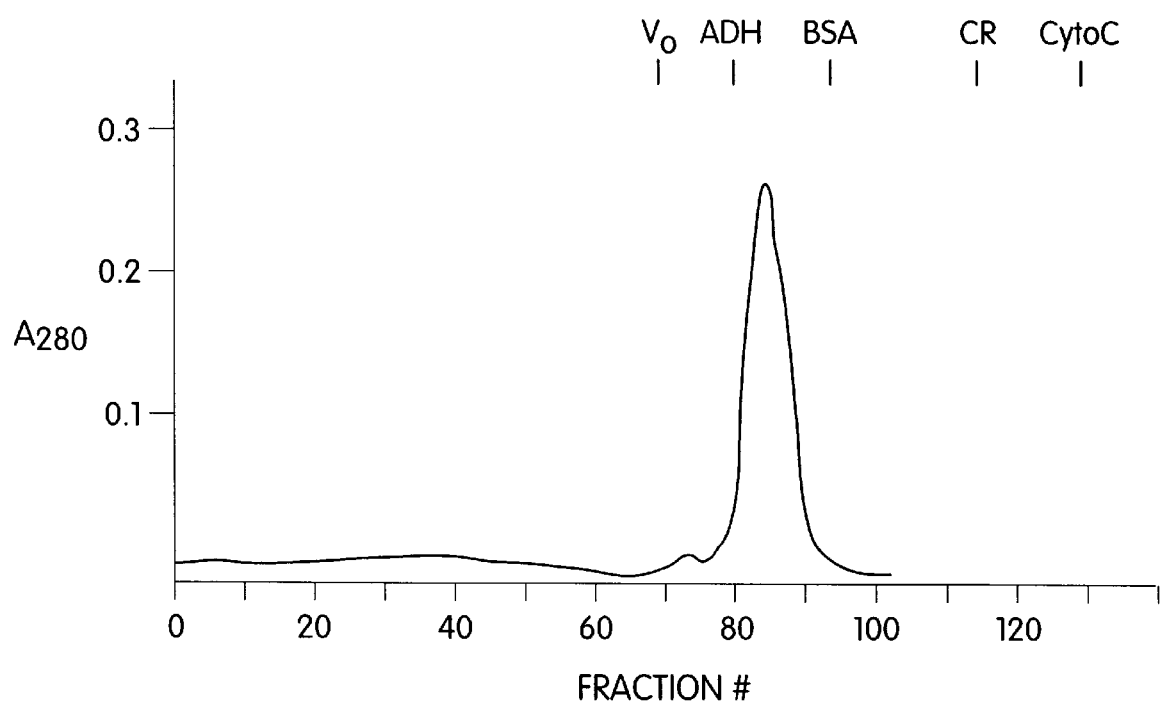
FIG. 3 is a gel filtration column elution profile of a soluble morphogen (OP-1) produced and purified from a mammalian cell culture by IMAC, S-Sepharose and S-200HR chromatography in TBS (Tris-buffered saline), wherein $V_O$ is the void volume, ADH is alcohol dehydrogenase (MW 150 kDa), BSA is bovine serum albumin (MW 67 kDa), CA is carbonic anhydrase (MW 29 kDa) and CytC is cytochrome C (MW 12.5 kDa).

FIG. 3 shows the absorbance profile at 280 nm. The soluble OP-1 complex elutes with an apparent molecular weight of 110 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

The complex components can be verified by running the complex-containing fraction from the S-200 or S200HR columns over a reverse phase C18 HPLC column and eluting in an acetonitrile gradient (in 0.1% TFA), using standard procedures. The complex is dissociated by this step, and the pro domain and mature species elute as separate species. These separate species then can be subjected to N-terminal sequencing using standard procedures (see, for example, *Guide to Protein Purification*, M. Deutscher, ed., Academic Press, San Diego, 1990, particularly pp. 602–613), and the identity of the isolated 36 kD, 39 kDa proteins confirmed as mature morphogen and isolated, cleaved pro domain, respectively. N-terminal sequencing of the isolated pro domain from mammalian cell produced OP-1 revealed 2 forms of the pro region, the intact form (beginning at residue 30 of Seq. ID No. 1) and a truncated form, (beginning at residue 48 of Seq. ID No. 1.) N-terminal sequencing of the polypeptide subunit of the isolated mature species reveals a range of N-termini for the mature sequence, beginning at residues 293, 300, 313, 315, 316, and 318, of Seq. ID No. 1, all of which are active as demonstrated by the standard bone induction assay.

V. In Vitro Soluble Morphogen Complex Formation

As an alternative to purifying soluble complexes from culture media or a body fluid, soluble complexes may be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding conditions. The concentration of denaturant in the solution then is decreased in a controlled, preferably step-wise manner, so as to allow proper refolding of the dimer and pro regions while maintaining the association of the pro domain with the dimer. Useful denaturants include 4–6 M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2 M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text one the subject is *Guide to Protein Purification*, M. Deutscher, ed., Academic Press, San Diego, 1990, particularly section V. Complex formation also may be aided by addition of one or more chaperone proteins.

VI. Stability of Soluble Morphogen Complexes

The stability of the highly purified soluble morphogen complex in a physiological buffer, e.g., tris-buffered saline (TBS) and phosphate-buffered saline (PBS), can be enhanced by any of a number of means. Currently preferred is by means of a pro region that comprises at least the first 18 amino acids of the pro sequence (e.g., residues 30–47 of Seq. ID NO. 1 for OP-1), and preferably is the full length pro region. Residues 30–47 show sequence homology to the N-terminal portion of other morphogens and are believed to have particular utility in enhancing complex stability for all morphogens. Other useful means for enhancing the stability of soluble morphogen complexes include three classes of additive. These additives include basic amino acids (e.g., L-arginine, lysine and betaine); nonionic detergents (e.g., Tween 80 or NonIdet P-120); and carrier proteins (e.g., serum albumin and casein). These additives include 1–100 mM, preferably 10–70 mM, including 50 mM, basic amino acid;, 0.01–1.0%, preferably 0.05–0.2%, including 0.1% (v/v) nonionic detergent;, and 0.01–1.0%, preferably 0.05–0.2%, including 0.1% (w/v) carrier protein.

VII. Activity of Soluble Morphogen Complex

Association of the pro domain with the mature dimeric species does not interfere with the morphogenic activity of the protein in vivo as demonstrated by different activity assays. Specifically, soluble OP-1 complex provided in a standard rat osteopenia model induces significant increase in bone growth and osteocalcin production (see Table II, below), in a mannor analogous to the results obtained using mature morphogen.

The assay is analogous to the osteoporosis model described in U.S. Ser. No. 923,780, but uses aged female rats rather than ovariectomized animals. Briefly, young or aged female rats (Charles River Labs, 115–145, and 335–460 g body weight, respectively) were dosed daily for 7 days by intravenous tail injection, with either 20 $\mu$g/Kg body weight soluble OP-1, or 100 $\mu$g/Kg body weight soluble OP-1. Control groups of young and aged female rats were dosed only with tris-buffered saline (TBS). Water and food were provided to all animals ad libitum. After 14 days, animals were sacrificed, and new bone growth measured by standard histometric procedures. Osteocalcin concentrations in serum also were measured. No detrimental effects of morphogen administration were detected as determined by changes in animal body or organ weight or by hematology profiles.

TABLE II

| No. Animals | Animal Group | Bone Area (B.Ar/T.Ar) | Osteocalcin (ng/ml) |
| --- | --- | --- | --- |
| 4 | Control | 5.50 ± 0.64 | 11.89 ± 4.20 |
| 5 | Aged female, 20 $\mu$g/Kg sol. OP-1 | 7.68 ± 0.63** | 22.24 ± 2.28** |
| 5 | Aged female, 100 $\mu$g/Kg sol. OP-1 | 9.82 ± 3.31* | 20.87 ± 6.14* |

*P < 0.05
**P < 0.01

Similar experiments performed using soluble OP-1 complex in the osteoporosis model described in U.S. Ser. No. 923,780 and incorporated hereinabove by reference using ovariectomized rats also show no detrimental effect using the complex form.

Both mature and soluble morphogen also can induce CAM (cell adhesion molecule) expression, as described in copending U.S. Ser. No. 07/022,813, filed Jul. 31, 1992, the disclosure of which is incorporated hereinabove by reference.

Briefly, and as described therein, induction of N-CAM isoforms (N-CAM-180, N-CAM-140 and N-CAM-120) can be monitored by reaction with the commercially available antibody mAb H28.123 (Sigma Co., St. Louis) and standard Western blot analysis (see, for example, *Molecular Cloning, A Laboratory Manual*, Sambrook et al. eds. Cold Spring Harbor Press, New York, 1989, particularly Section 18). Incubation of a growing culture of transformed cells of neuronal origin, NG108-15 cels (ATCC, Rockville, Md.) with either mature morphogen dimers or soluble morphogen complexes (10–100 ng/ml, preferably at least 40 ng/ml) induces a redifferentiation of these cells back to a morphology characteristic of untransformed neurons, including specific induction and/or enhanced expression of all 3 N-CAM isoforms. In the experiment, cells were subcultured on poly-L-lysine coated 6-well plates and grown in chemically defined medium for 2 days before the experiment. Fresh aliquots of morphogen were added (2.5 µl) daily.

VIII. Antibody Production

Provided below are standard protocols for polyclonal and monoclonal antibody production. For antibodies which recognize the soluble complex only, preferably the isolated pro region is used as the antigen; where antibodies specific to the mature protein are desired, the antigen preferably comprises at least the C-terminal domain or the intact mature sequence.

Polyclonal antibody may be prepared as follows. Each rabbit is given a primary immunization of 100 µg/500 µl of antigen, in 0.1% SDS mixed with 500 µl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against the morphogen antigen is detected in the serum using an ELISA assay. Then, the rabbit is boosted monthly with 100 µg of antigen and bled (15 ml per bleed) at days seven and ten after boosting.

Monoclonal antibody specific for a given morphogen may be prepared as follows. A mouse is given two injections of the morphogen antigen. The protein or protein fragment preferably is recombinantly produced. The first injection contains 100 µg of antigen in complete Freund's adjuvant and is given subcutaneously. The second injection contains 50 µg of antigen in incomplete adjuvant and is given intraperitoneally. The mouse then receives a total of 230 µg of OP-3 in four intraperitoneal injections at various times over an eight month period. One week prior to fusion, the mouse is boosted intraperitoneally with antigen (e.g., 100 µg) and may be additionally boosted with a peptide fragment conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for mature or soluble morphogenspecific antibodies using the appropriate portion of the morphogen sequence as antigen. The cell fusion and monoclonal screening steps readily are performed according to standard procedures well described in standard texts widely available in the art.

Using these standard procedures, anti-pro domain antisera was prepared from rabbits using the isolated pro domain from OP-1 as the antigen, and monoclonal antibody ("mAb") to the mature domain was produced in mice, using an *E. coli*-produced truncated form of OP-1 as antigen.

Standard Western blot analysis performed under reducing conditions demonstrates that the anti-pro domain antisera ("anti-pro") is specific for the pro domain only, while the mAb to mature OP-1 ("anti-mature OP-1") is specific for the dimer subunits, that the two antibodies do not cross-react, and that the antibodies and can be used to distinguish between soluble and mature protein forms in a sample, e.g., of conditioned media or serum. A tabular representation of the Western blot results is in Table III below, where reactivity of mAb to mature OP-1 is indicated by "yy", and reactivity of the anti-pro antisera is indicated by "xx".

TABLE III

| Antibody | Purified Sol OP1 | Conditioned CHO Cell Media | Isolated Pro Domain | Purified Dimer Subunits |
|---|---|---|---|---|
| "anti-pro" | xx | xx | xx | |
| "anti-mature OP-1" | yy | yy | | yy |

IX. Immunoassays

The ability to detect morphogens in solution and to distinguish between soluble and mature dimeric morphogen forms provides a valuable tool for diagnostic assays, allowing one to monitor the level and type of morphogen free in the body, e.g., in serum and other body fluids.

For example, OP-1 is an intimate participant in normal bone growth and resorption. Thus, soluble OP-*1* is expected to be detected at higher concentrations in individuals experiencing high bone turnover, such as children, and at substantially lower levels in individuals with abnormally low rates of bone turnover, such as patients with osteoporosis, osteosarcoma, Paget's disease and the like. Monitoring the level of OP-1, or other bone targeted morphogens such as BMP2 and BMP4, in serum thus provides a means for evaluating the status of bone tissue in an individual, as well as a means for monitoring the efficacy of a treatment to regenerate damaged or lost bone tissue. Similarly, monitoring the level of endogenous GDF-1, can provide diagnostic information on the health of nerve tissue, particularly brain tissue. Moreover, following this disclosure one can distinguish between the level of soluble and mature forms in solution.

A currently preferred detection means for evaluating the level of morphogen in a body fluid comprises an immunoassay utilizing an antibody or other suitable binding protein capable of reacting specifically with a morphogen and being detected as part of a complex with the morphogen. Immunoassays may be performed using standard techniques known in the art and antibodies raised against a morphogen and specific for that morphogen. Antibodies which recognize a morphogen protein form of interest may be generated as described herein and these antibodies then used to monitor endogenous levels of protein in a body fluid, such as serum, whole blood or peritoneal fluid. To monitor endogenous concentrations of soluble morphogen, the antibody chosen preferably has binding specificity for the soluble form e.g., has specificity for the pro domain. Such antibodies may be generated by using the pro domain or a portion thereof as the antigen, essentially as described herein. A suitable pro domain for use as an antigen may be obtained by isolating the soluble complex and then separating the noncovalently associated pro domain from the mature domain using standard procedures, e.g., by passing the complex over an HPLC column, as described above or by separation by gel electrophoresis. Alternatively, the pro form of the protein in its monomeric form may be used as the antigen and the candidate antibodies screened by Western blot or other standard immunoassay for those which recognize the pro domain of the soluble form of the protein of interest, but not the mature form, also as described above.

Monomeric pro forms can be obtained from cell lysates of CHO produced cells, or from prokaryotic expression of a DNA encoding the pro form, in for example, *E. coli*. The pro form, which has an apparent molecular weight of about 50 kDa in mammalian cells, can then be isolated by HPLC and/or by gel electrophoresis, as described above.

In order to detect and/or quantitate the amount of morphogenic protein present in a solution, an immunoassay may be performed to detect the morphogen using a polyclonal or monoclonal antibody specific for that protein. Here, soluble and mature forms of the morphogen also may be distinguished by using antibodies that discriminate between the two forms of the proteins as described above. Currently preferred assays include ELISAS and radioimmunassays, including standard competitor assays useful for quantitating the morphogen in a sample, where an unknown amount of sample morphogen is allowed to react with anti-morphogen antibody and this interaction is competed with a known amount of labeled antigen. The level of bound or free labeled antigen at equilibrium then is measured to quantitate the amount of unlabeled antigen in solution, the amount of sample antigen being proportional to the amount of free labeled antigen. Exemplary protocols for these assays are provided below. However, as will be appreciated by those skilled in the art, variations of these protocols, as well as other immunoassays, are well known in the literature and within the skill of the art. For example, in the ELISA protocol provided below, soluble OP-1 is identified in a sample using biotinylated anti-pro antiserum. Biotinylated antibodies can be visualized in a colormetric assay or in a chemiluminescent assay, as described below. Alternatively, the antibody can be radio-labeled with a suitable molecule, such as $^{125}$I. Still another protocol that may be used is a solid phase immunoassay, preferably using an affinity column with anti-morphogen antibody complexed to the matrix surface and over which a serum sample may be passed. A detailed description of useful immunoassays, including protocols and general considerations is provided in, for example, *Molecular Cloning: A Laboratory Manual*, Sambrook et al., eds. Cold Spring Harbor Press, New York, 1989, particularly Section 18.

For serum assays, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble morphogen complex or mature morphogens relative to that of the other proteins present in serum. Further purification also can be achieved by chromatographic techniques well known in the art.

Soluble OP-1 may be detected using a polyclonal antibody specific for the OP-1 pro domain in an ELISA, as follows. 1 µg/100 µl of affinity-purified polyclonal rabbit IgG specific for OP-1-pro is added to each well of a 96-well plate and incubated at 37° C. for an hour. The wells are washed four times with 0.167 M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant or serum sample is added to each well in triplicate and incubated at 37° C. for 30 min. After incubation, 100 µl biotinylated rabbit anti-pro serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 µl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5 M Tris buffered Saline (TBS), pH 7.2. 50 µl substrate (ELISA Amplification System Kit, Life Technologies, Inc., Bethesda, Md.) is added to each well incubated at room temperature for 15 min. Then, 50 µl amplifier (from the same amplification system kit) is added and incubated for another 15 min at room temperature. The reaction is stopped by the addition of 50 µl 0.3 M sulphuric acid. The OD at 490 nm of the solution in each well is recorded. To quantitate the level of soluble OP-1 in the sample, a standard curve is performed in parallel with the test samples. In the standard curve, known increasing amounts of purified OP-1-pro is added. Alternatively, using, for example, Lumi-phos 530 (Analytical Luminescence Laboratories) as the substrate and detection at 300–650 nm in a standard luminometer, complexes can be detected by chemiluminescence, which typically provides a more sensitive assay than detection by means of a visible color change.

Morphogen (soluble or mature form) may be detected in a standard plated-based radioimmunoassay as follows. Empirically determined limiting levels of anti-morphogen antibody (e.g., anti-OP-1, typically 50–80 ng/well) are bound to wells of a PVC plate e.g., in 50 µl PBS phosphate buffered saline. After sufficient incubation to allow binding at room temperature, typically one hour, the plate is washed in a PBS/Tween 20 solution, ("washing buffer"), and 200 µl of block (3% BSA, 0.1 µ lysine in 1×BSB) is added to each well and allowed to incubate for 1 hour, after which the wells are washed again in washing buffer. 40 µl of a sample composed of serially diluted plasma (preferably partially purified as described above) or morphogen standard (e.g., OP-1) is added to wells in triplicate. Samples preferably are diluted in PTTH (15 mM KH$_2$PO$_4$, 8 mM Na$_2$PO$_4$, 27 mM KCl, 137 mM NaCl, 0.05% Tween 20, 1 mg/ml HSA, 0.05% NaN$_3$, pH 7.2). 10 µl of labelled competitor antigen, preferably 100,000–500,000 cpm/sample is added (e.g., $^{125}$I OP-1, radiolabelled using standard procedures), and plates are incubated overnight at 4° C. Plates then are washed in washing buffer, and allowed to dry. Wells are cut apart and bound labelled OP-1 counted in a standard gamma counter. The quantities of bound labelled antigen (e.g., $^{125}$I OP-1) measured in the presence and absence of sample then are compared, the difference being proportional to the amount of sample antigen (morphogen) present in the sample fluid.

As a corollary assay method, immunoassays may be developed to detect endogenous anti-morphogen antibodies, and to distinguish between such antibodies to soluble or mature forms. Endogenous anti-morphogen antibodies have been detected in serum, and their level is known to increase, for example, upon implanting of an osteogenic device in a mammal. Without being limited to a particular theory, these antibodies may play a role in modulating morphogen activity by modulating the level of available protein in serum. Assays that monitor the level of endogenous antibodies in blood or their body fluids thus can be used in diagnostic assays to evaluate the status of a tissue, as well as to provide a means for monitoring the efficacy of a therapy for tissue regeneration.

The currently preferred means for detecting endogenous anti-morphogen antibodies is by means of a standard Western blot. See, for example, *Molecular Cloning: A Laboratory Manual* Sambrook et al., eds., Cold Spring Harbor Press, New York, 1989, particularly pages 18.60–18.75, incorporated herein by reference, for a detailed description of these assays. Purified mature or soluble morphogen is electrophoresed on an SDS polyacrylamide gel under oxidized or reduced conditions designed to separate the proteins in solution, and the proteins then transferred to a polyvinylidene difluoride microporus membrane (0.45 μm pore sizes) using standard buffers and procedures. The filter then is incubated with the serum being tested (at various dilutions). Antibodies bound to either the pro domain or the mature morphogen domain are detected by means of an anti-human antibody protein, e.g., goat anti-human Ig. Titers of the antimorphogen antibodies can be determined by further dilution of the serum until no signal is detected.

X. Formulations and Methods for Administering Soluble Morphogens as Therapeutic Agents The soluble morphogens of this invention are particularly useful as therapeutic agents to regenerate diseased or damaged tissue in a mammal, particularly a human.

The soluble morphogen complexes may be used to particular advantage in regeneration of damaged or diseased lung, heart, liver, kidney, nerve or pancreas tissue, as well as in the transplantation and/or grafting of these tissues and bone marrow, skin, gastrointestinal mucosa, and other living tissues.

The soluble morphogen complexes described herein may be provided to an individual by any suitable means, preferably directly or systemically, e.g., parenterally or orally. Where the morphogen is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the soluble morphogen complex preferably comprises part of an aqueous solution. The solution is physiologically acceptable so that in addition to delivery of the desired morphogen to the patient, the solution does not otherwise adversely affect the patient's electrolyte and volume balance. The aqueous medium for the soluble morphogen thus may comprise normal physiologic saline (0.9% NaCl, 0.15 M), pH 7–7.4.

Soluble morphogens of this invention are readily purified from cultured cell media into a physiological buffer, as described above. In addition, and as described above, if desired, the soluble complexes may be formulated with one or more additional additives, including basic amino acids (e.g., L-arginine, lysine, betaine); non-ionic detergents (e.g. Tween-80 or NonIdet-120) and carrier proteins (e.g., serum albumin and casein).

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the soluble morphogen in vivo.

Other potentially useful parenteral delivery systems for these morphogens include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

The soluble morphogens described herein also may be administered orally. Oral administration of proteins as therapeutics generally is not practiced as most proteins readily are degraded by digestive enzymes and acids in the mammalian digestive system before they can be absorbed into the bloodstream. However, the mature domains of the morphogens described herein typically are acid-stable and protease-resistant (see, for example, U.S. Pat. No. 4,968,590.) In addition, at least one morphogen, OP-1, has been identified, in mammary gland extract, colostrum and milk, as well as saliva. Moreover, the OP-1 purified from mammary gland extract is morphogenically active. For example, this protein induces endochondral bone formation in mammals when implanted subcutaneously in association with a suitable matrix material, using a standard in vivo bone assay, such as is disclosed in U.S. Pat. No. 4,968,590. In addition, endogenous morphogen also is detected in human serum (see above). Finally, comparative experiments with soluble and mature morphogens in a number of experiments defining morphogenic activity indicate that the non-covalent association of the pro domain with the dimeric species does not interfere with morphogenic activity. These findings indicate that oral and parenteral administration are viable means for administering morphogens to an individual, and that soluble morphogens have utility in systemic administration protocols.

The soluble complexes provided herein also may be associated with molecules capable of targeting the morphogen to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting soluble morphogens to bone tissue. Alternatively, an antibody or other binding protein that interacts specifically with a surface molecule on the desired target tissue cells also may be used. Such targeting molecules further may be covalently associated to the morphogen complex, e.g., by chemical crosslinking, or by using standard genetic engineering means to create, for example, an acid labile bond such as an Asp-Pro linkage. Useful targeting molecules may be designed, for example, using the single chain binding site technology disclosed, for example, in U.S. Pat. No. 5,091,513.

Finally, the soluble morphogen complexes provided herein may be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface.

The compositions can be formulated for parenteral or oral administration to humans or other mammals in therapeutically effective amounts, e.g., amounts which provide appropriate concentrations of the morphogen to target tissue for a time sufficient to induce morphogenesis, including particular steps thereof, as described above.

Where the soluble morphogen complex is to be used as part of a transplant procedure, the morphogen may be provided to the living tissue or organ to be transplanted prior to removal of the tissue or organ from the donor. The morphogen may be provided to the donor host directly, as by injection of a formulation comprising the soluble complex into the tissue, or indirectly, e.g., by oral or parenteral administration, using any of the means described above.

Alternatively or, in addition, once removed from the donor, the organ or living tissue may be placed in a preservation solution containing the morphogen. In addition, the recipient also preferably is provided with the morphogen just prior to, or concommitant with, transplantation. In all cases, the soluble complex may be administered directly to the tissue at risk, as by injection to the tissue, or it may be provided systemically, either by oral or parenteral administration, using any of the methods and formulations described herein and/or known in the art.

Where the morphogen comprises part of a tissue or organ preservation solution, any commercially available preservation solution may be used to advantage. A useful preservation solution is described in U.S. Ser. No. 07/938,337, filed Aug. 28, 1992, and in PCT/US92/07358, both incorporated herein by reference.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the compounds of this invention may be provided in an aqueous physiological buffer solution containing about 0.001 to 10% w/v compound for parenteral administration. Typical dose ranges are from about 10 ng/kg to about 1 g/kg of body weight per day; a preferred dose range is from about 0.1 $\mu$g/kg to 100 mg/kg of body weight. No obvious morphogen-induced pathological lesions are induced when mature morphogen (e.g., OP-1, 20 $\mu$g) is administered daily to normal growing rats for 21 consecutive days. Moreover, 10 $\mu$g systemic injections of morphogen (e.g., OP-1) injected daily for 10 days into normal newborn mice does not produce any gross abnormalities.

Where morphogens are administered systemically, in the methods of the present invention, preferably a large volume loading dose is used at the start of the treatment. The treatment then is continued with a maintenance dose. Further administration then can be determined by monitoring at intervals the levels of the morphogen in the blood.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for evaluating a disease state caused by a morphogen imbalance, the method comprising
comparing in a tissue or body fluid sample a detected amount to an expected amount of a compound selected from the group consisting of:
  (a) a soluble morphogen complex comprising a dimeric morphogenic protein having an amino acid sequence selected from the group consisting of:
    (i) a sequence having at least 70% homology with the C-terminal seven-cysteine skeleton of human OP-1, residues 330–431 of SEQ. ID NO. 1, and
    (ii) Generic Sequence 7, SEQ. ID NO. 20;
wherein said dimeric morphogenic protein is in non-covalent association with a morphogen pro region or fragment thereof.

2. A method for evaluating the efficacy of a therapy for regenerating lost or damaged tissue in a mammal, the method comprising comparing in a tissue or body fluid sample a detected amount to an expected amount of a compound selected from the group consisting of:
  (a) a soluble morphogen complex comprising a dimeric morphogenic protein having an amino acid sequence selected from the group consisting of:
    (i) a sequence having at least 70% homology with the C-terminal seven-cysteine skeleton of human OP-1, residues 330–431 of SEQ. ID NO. 1, and
    (ii) Generic Sequence 7, SEQ. ID NO. 20; in non-covalent association with a morphogen pro region or fragment thereof.

3. A method for diagnosing a tissue disorder in a mammal, the method comprising comparing in a tissue or body fluid sample a detected amount to an expected amount of a compound selected from the group consisting of:
  (a) a soluble morphogen complex comprising a dimeric morphogenic protein having an amino acid sequence selected from the group consisting of:
    (i) a sequence having at least 70% homology with the C-terminal seven-cysteine skeleton of human OP-1, residues 330–431 of SEQ. ID NO. 1, and
    (ii) Generic Sequence 7, SEQ. ID NO. 20; in non-covalent association with a morphogen pro region or fragment thereof.

4. The method of claim 1, 2, or 3 wherein said pro region is obtained from a bone morphogenic protein comprising at least 100 amino acids sharing at least 70% amino acid sequence homology with residues 330–431 of SEQ. ID. NO. 1 (human OP-1).

5. The method of claim 3 wherein said tissue disorder is a bone tissue disorder.

6. The assay of claim 5 wherein said bone tissue disorder is selected from the group consisting of osteosarcoma, osteoporosis, and Paget's disease.

7. The method of claim 6 wherein said method is an immunoassay.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: HOMO SAPIENS
    ( F ) TISSUE TYPE: HIPPOCAMPUS ( i x ) FEATURE:
    ( A ) NAME/KEY: CDS
    ( B ) LOCATION: 49..1341
    ( C ) IDENTIFICATION METHOD: experimental
    ( D ) OTHER INFORMATION: /function="OSTEOGENIC PROTEIN"
        / product= "OP1"
        / evidence= EXPERIMENTAL
        / standard_name= "OP1"

( x i ) SEQUENCE DESCRIPTION: SEQ ID NO:1:

```
GGTGCGGGCC  CGGAGCCCGG  AGCCCGGGTA  GCGCGTAGAG  CCGGCGCG ATG CAC GTG                57
                                                         Met His Val
                                                          1

CGC TCA CTG CGA GCT GCG GCG CCG CAC AGC TTC GTG GCG CTC TGG GCA                   105
Arg Ser Leu Arg Ala Ala Ala Pro His Ser Phe Val Ala Leu Trp Ala
     5              10                  15

CCC CTG TTC CTG CTG CGC TCC GCC CTG GCC GAC TTC AGC CTG GAC AAC                   153
Pro Leu Phe Leu Leu Arg Ser Ala Leu Ala Asp Phe Ser Leu Asp Asn
 20              25                  30                  35

GAG GTG CAC TCG AGC TTC ATC CAC CGG CGC CTC CGC AGC CAG GAG CGG                   201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC                   249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG                   297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC                   345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC                   393
Gly Gln Gly Phe Ser Tyr Pro Tyr Lys Ala Val Phe Ser Thr Gln Gly
100             105                 110                 115

CCC CCT CTG GCC AGC CTG CAA GAT AGC CAT TTC CTC ACC GAC GCC GAC                   441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC                   489
Met Val Met Ser Phe Val Asn Leu Val Glu His Asp Lys Glu Phe Phe
                    135                 140                 145

CAC CCA CGC TAC CAC CAT CGA GAG TTC CGG TTT GAT CTT TCC AAG ATC                   537
His Pro Arg Tyr His His Arg Glu Phe Arg Phe Asp Leu Ser Lys Ile
            150                 155                 160

CCA GAA GGG GAA GCT GTC ACG GCA GCC GAA TTC CGG ATC TAC AAG GAC                   585
Pro Glu Gly Glu Ala Val Thr Ala Ala Glu Phe Arg Ile Tyr Lys Asp
        165                 170                 175

TAC ATC CGG GAA CGC TTC GAC AAT GAG ACG TTC CGG ATC AGC GTT TAT                   633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC                   681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC                   729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG                   777
Ile Thr Ala Thr Ser Asn His Trp Val Val Asn Pro Arg His Asn Leu
        230                 235                 240
```

-continued

| | | | | | | | | | | | | | | | | |
|---|---|---|---|---|---|---|---|---|---|---|---|---|---|---|---|---|
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro | |
| | | 245 | | | | 250 | | | | | 255 | | | | | |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile | |
| | | | | 280 | | | | | 285 | | | | | 290 | | |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro | |
| | | | 295 | | | | 300 | | | | | 305 | | | | |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser | |
| | | 310 | | | | 315 | | | | | 320 | | | | | |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe | |
| 325 | | | | | 330 | | | | | 335 | | | | | | |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala | |
| 340 | | | | | 345 | | | | | 350 | | | | | 355 | |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met | |
| | | | | 360 | | | | | 365 | | | | | 370 | | |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn | |
| | | | 375 | | | | 380 | | | | | 385 | | | | |
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala | |
| | | 390 | | | | 395 | | | | | 400 | | | | | |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys | |
| 405 | | | | | 410 | | | | | 415 | | | | | | |
| TAC | AGA | AAC | ATG | GTG | GTC | CGG | GCC | TGT | GGC | TGC | CAC | TAGCTCCTCC | | | | 1351 |
| Tyr | Arg | Asn | Met | Val | Val | Arg | Ala | Cys | Gly | Cys | His | | | | | |
| 420 | | | | 425 | | | | | 430 | | | | | | | |

| | | | | |
|---|---|---|---|---|
| GAGAATTCAG | ACCCTTTGGG | GCCAAGTTTT | TCTGGATCCT | CCATTGCTCG | CCTTGGCCAG | 1411 |
| GAACCAGCAG | ACCAACTGCC | TTTTGTGAGA | CCTTCCCCTC | CCTATCCCCA | ACTTTAAAGG | 1471 |
| TGTGAGAGTA | TTAGGAAACA | TGAGCAGCAT | ATGGCTTTTG | ATCAGTTTTT | CAGTGGCAGC | 1531 |
| ATCCAATGAA | CAAGATCCTA | CAAGCTGTGC | AGGCAAAACC | TAGCAGGAAA | AAAAAACAAC | 1591 |
| GCATAAAGAA | AAATGGCCGG | GCCAGGTCAT | TGGCTGGGAA | GTCTCAGCCA | TGCACGGACT | 1651 |
| CGTTTCCAGA | GGTAATTATG | AGCGCCTACC | AGCCAGGCCA | CCCAGCCGTG | GGAGGAAGGG | 1711 |
| GGCGTGGCAA | GGGGTGGGCA | CATTGGTGTC | TGTGCGAAAG | GAAAATTGAC | CCGGAAGTTC | 1771 |
| CTGTAATAAA | TGTCACAATA | AAACGAATGA | ATGAAAAAAA | AAAAAAAAA A | | 1822 |

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | His | Val | Arg | Ser | Leu | Arg | Ala | Ala | Ala | Pro | His | Ser | Phe | Val | Ala |
| 1 | | | | 5 | | | | | 10 | | | | | 15 | |

| | | | | | | | | | | | | | |
|---|---|---|---|---|---|---|---|---|---|---|---|---|---|
| Leu | Trp | Ala | Pro 20 | Leu | Phe | Leu | Leu | Arg 25 | Ser | Ala | Leu | Ala 30 | Asp | Phe | Ser |

Leu Trp Ala Pro Leu Phe Leu Leu Arg Ser Ala Leu Ala Asp Phe Ser
                20                    25              30

Leu Asp Asn Glu Val His Ser Ser Phe Ile His Arg Arg Leu Arg Ser
        35              40                  45

Gln Glu Arg Arg Glu Met Gln Arg Glu Ile Leu Ser Ile Leu Gly Leu
    50              55                      60

Pro His Arg Pro Arg Pro His Leu Gln Gly Lys His Asn Ser Ala Pro
65              70                      75                      80

Met Phe Met Leu Asp Leu Tyr Asn Ala Met Ala Val Glu Glu Gly Gly
            85                  90                      95

Gly Pro Gly Gly Gln Gly Phe Ser Tyr Pro Tyr Lys Ala Val Phe Ser
            100             105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
            245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

( 2 ) INFORMATION FOR SEQ ID NO:3:

( i ) SEQUENCE CHARACTERISTICS:
    ( A ) LENGTH: 1873 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 104..1393
    ( D ) OTHER INFORMATION: /function="OSTEOGENIC PROTEIN"
        / product= "MOP1"
        / note= "MOP1 CDNA"

( x i ) SEQUENCE DESCRIPTION: SEQ ID NO:3:

```
CTGCAGCAAG  TGACCTCGGG  TCGTGGACCG  CTGCCCTGCC  CCCTCCGCTG  CCACCTGGGG                60

CGGCGCGGGC  CCGGTGCCCC  GGATCGCGCG  TAGAGCCGGC  GCG  ATG  CAC  GTG  CGC               115
                                                    Met  His  Val  Arg
                                                     1

TCG  CTG  CGC  GCT  GCG  GCG  CCA  CAC  AGC  TTC  GTG  GCG  CTC  TGG  GCG  CCT       163
Ser  Leu  Arg  Ala  Ala  Ala  Pro  His  Ser  Phe  Val  Ala  Leu  Trp  Ala  Pro
 5                       10                       15                       20

CTG  TTC  TTG  CTG  CGC  TCC  GCC  CTG  GCC  GAT  TTC  AGC  CTG  GAC  AAC  GAG       211
Leu  Phe  Leu  Leu  Arg  Ser  Ala  Leu  Ala  Asp  Phe  Ser  Leu  Asp  Asn  Glu
                     25                       30                       35

GTG  CAC  TCC  AGC  TTC  ATC  CAC  CGG  CGC  CTC  CGC  AGC  CAG  GAG  CGG  CGG       259
Val  His  Ser  Ser  Phe  Ile  His  Arg  Arg  Leu  Arg  Ser  Gln  Glu  Arg  Arg
               40                       45                       50

GAG  ATG  CAG  CGG  GAG  ATC  CTG  TCC  ATC  TTA  GGG  TTG  CCC  CAT  CGC  CCG       307
Glu  Met  Gln  Arg  Glu  Ile  Leu  Ser  Ile  Leu  Gly  Leu  Pro  His  Arg  Pro
          55                       60                       65

CGC  CCG  CAC  CTC  CAG  GGA  AAG  CAT  AAT  TCG  GCG  CCC  ATG  TTC  ATG  TTG       355
Arg  Pro  His  Leu  Gln  Gly  Lys  His  Asn  Ser  Ala  Pro  Met  Phe  Met  Leu
     70                       75                       80

GAC  CTG  TAC  AAC  GCC  ATG  GCG  GTG  GAG  GAG  AGC  GGG  CCG  GAC  GGA  CAG       403
Asp  Leu  Tyr  Asn  Ala  Met  Ala  Val  Glu  Glu  Ser  Gly  Pro  Asp  Gly  Gln
85                       90                       95                      100

GGC  TTC  TCC  TAC  CCC  TAC  AAG  GCC  GTC  TTC  AGT  ACC  CAG  GGC  CCC  CCT       451
Gly  Phe  Ser  Tyr  Pro  Tyr  Lys  Ala  Val  Phe  Ser  Thr  Gln  Gly  Pro  Pro
                    105                      110                      115

TTA  GCC  AGC  CTG  CAG  GAC  AGC  CAT  TTC  CTC  ACT  GAC  GCC  GAC  ATG  GTC       499
Leu  Ala  Ser  Leu  Gln  Asp  Ser  His  Phe  Leu  Thr  Asp  Ala  Asp  Met  Val
               120                      125                      130

ATG  AGC  TTC  GTC  AAC  CTA  GTG  GAA  CAT  GAC  AAA  GAA  TTC  TTC  CAC  CCT       547
Met  Ser  Phe  Val  Asn  Leu  Val  Glu  His  Asp  Lys  Glu  Phe  Phe  His  Pro
          135                      140                      145

CGA  TAC  CAC  CAT  CGG  GAG  TTC  CGG  TTT  GAT  CTT  TCC  AAG  ATC  CCC  GAG       595
Arg  Tyr  His  His  Arg  Glu  Phe  Arg  Phe  Asp  Leu  Ser  Lys  Ile  Pro  Glu
     150                      155                      160

GGC  GAA  CGG  GTG  ACC  GCA  GCC  GAA  TTC  AGG  ATC  TAT  AAG  GAC  TAC  ATC       643
Gly  Glu  Arg  Val  Thr  Ala  Ala  Glu  Phe  Arg  Ile  Tyr  Lys  Asp  Tyr  Ile
165                      170                      175                      180

CGG  GAG  CGA  TTT  GAC  AAC  GAG  ACC  TTC  CAG  ATC  ACA  GTC  TAT  CAG  GTG       691
Arg  Glu  Arg  Phe  Asp  Asn  Glu  Thr  Phe  Gln  Ile  Thr  Val  Tyr  Gln  Val
                    185                      190                      195

CTC  CAG  GAG  CAC  TCA  GGC  AGG  GAG  TCG  GAC  CTC  TTC  TTG  CTG  GAC  AGC       739
Leu  Gln  Glu  His  Ser  Gly  Arg  Glu  Ser  Asp  Leu  Phe  Leu  Leu  Asp  Ser
               200                      205                      210

CGC  ACC  ATC  TGG  GCT  TCT  GAG  GAG  GGC  TGG  TTG  GTG  TTT  GAT  ATC  ACA       787
Arg  Thr  Ile  Trp  Ala  Ser  Glu  Glu  Gly  Trp  Leu  Val  Phe  Asp  Ile  Thr
          215                      220                      225
```

-continued

| | | | | | | | | | | | | | | | |
|---|---|---|---|---|---|---|---|---|---|---|---|---|---|---|---|
| GCC | ACC | AGC | AAC | CAC | TGG | GTG | GTC | AAC | CCT | CGG | CAC | AAC | CTG | GGC | TTA | 835
| Ala | Thr | Ser | Asn | His | Trp | Val | Val | Asn | Pro | Arg | His | Asn | Leu | Gly | Leu |
| | 230 | | | | 235 | | | | | | 240 | | | | |
| CAG | CTC | TCT | GTG | GAG | ACC | CTG | GAT | GGG | CAG | AGC | ATC | AAC | CCC | AAG | TTG | 883
| Gln | Leu | Ser | Val | Glu | Thr | Leu | Asp | Gly | Gln | Ser | Ile | Asn | Pro | Lys | Leu |
| 245 | | | | | 250 | | | | | 255 | | | | | 260 |
| GCA | GGC | CTG | ATT | GGA | CGG | CAT | GGA | CCC | CAG | AAC | AAG | CAA | CCC | TTC | ATG | 931
| Ala | Gly | Leu | Ile | Gly | Arg | His | Gly | Pro | Gln | Asn | Lys | Gln | Pro | Phe | Met |
| | | | | 265 | | | | | 270 | | | | | 275 | |
| GTG | GCC | TTC | TTC | AAG | GCC | ACG | GAA | GTC | CAT | CTC | CGT | AGT | ATC | CGG | TCC | 979
| Val | Ala | Phe | Phe | Lys | Ala | Thr | Glu | Val | His | Leu | Arg | Ser | Ile | Arg | Ser |
| | | | 280 | | | | | 285 | | | | | 290 | | |
| ACG | GGG | GGC | AAG | CAG | CGC | AGC | CAG | AAT | CGC | TCC | AAG | ACG | CCA | AAG | AAC | 1027
| Thr | Gly | Gly | Lys | Gln | Arg | Ser | Gln | Asn | Arg | Ser | Lys | Thr | Pro | Lys | Asn |
| | | 295 | | | | | 300 | | | | | 305 | | | |
| CAA | GAG | GCC | CTG | AGG | ATG | GCC | AGT | GTG | GCA | GAA | AAC | AGC | AGC | AGT | GAC | 1075
| Gln | Glu | Ala | Leu | Arg | Met | Ala | Ser | Val | Ala | Glu | Asn | Ser | Ser | Ser | Asp |
| | 310 | | | | | 315 | | | | | 320 | | | | |
| CAG | AGG | CAG | GCC | TGC | AAG | AAA | CAT | GAG | CTG | TAC | GTC | AGC | TTC | CGA | GAC | 1123
| Gln | Arg | Gln | Ala | Cys | Lys | Lys | His | Glu | Leu | Tyr | Val | Ser | Phe | Arg | Asp |
| 325 | | | | | 330 | | | | 335 | | | | | 340 | |
| CTT | GGC | TGG | CAG | GAC | TGG | ATC | ATT | GCA | CCT | GAA | GGC | TAT | GCT | GCC | TAC | 1171
| Leu | Gly | Trp | Gln | Asp | Trp | Ile | Ile | Ala | Pro | Glu | Gly | Tyr | Ala | Ala | Tyr |
| | | | | 345 | | | | | 350 | | | | | 355 | |
| TAC | TGT | GAG | GGA | GAG | TGC | GCC | TTC | CCT | CTG | AAC | TCC | TAC | ATG | AAC | GCC | 1219
| Tyr | Cys | Glu | Gly | Glu | Cys | Ala | Phe | Pro | Leu | Asn | Ser | Tyr | Met | Asn | Ala |
| | | | 360 | | | | | 365 | | | | | 370 | | |
| ACC | AAC | CAC | GCC | ATC | GTC | CAG | ACA | CTG | GTT | CAC | TTC | ATC | AAC | CCA | GAC | 1267
| Thr | Asn | His | Ala | Ile | Val | Gln | Thr | Leu | Val | His | Phe | Ile | Asn | Pro | Asp |
| | | 375 | | | | | 380 | | | | | 385 | | | |
| ACA | GTA | CCC | AAG | CCC | TGC | TGT | GCG | CCC | ACC | CAG | CTC | AAC | GCC | ATC | TCT | 1315
| Thr | Val | Pro | Lys | Pro | Cys | Cys | Ala | Pro | Thr | Gln | Leu | Asn | Ala | Ile | Ser |
| | 390 | | | | 395 | | | | | 400 | | | | | |
| GTC | CTC | TAC | TTC | GAC | GAC | AGC | TCT | AAT | GTC | ATC | CTG | AAG | AAG | TAC | AGA | 1363
| Val | Leu | Tyr | Phe | Asp | Asp | Ser | Ser | Asn | Val | Ile | Leu | Lys | Lys | Tyr | Arg |
| 405 | | | | | 410 | | | | | 415 | | | | | 420 |
| AAC | ATG | GTG | GTC | CGG | GCC | TGT | GGC | TGC | CAC | TAGCTCTTCC | TGAGACCCTG | | | | | 1413
| Asn | Met | Val | Val | Arg | Ala | Cys | Gly | Cys | His | | | | | | |
| | | | | 425 | | | | | 430 | | | | | | |

| | | | | |
|---|---|---|---|---|
| ACCTTTGCGG | GGCCACACCT | TTCCAAATCT | TCGATGTCTC | ACCATCTAAG | TCTCTCACTG | 1473
| CCCACCTTGG | CGAGGAGAAC | AGACCAACCT | CTCCTGAGCC | TTCCCTCACC | TCCCAACCGG | 1533
| AAGCATGTAA | GGGTTCCAGA | AACCTGAGCG | TGCAGCAGCT | GATGAGCGCC | CTTTCCTTCT | 1593
| GGCACGTGAC | GGACAAGATC | CTACCAGCTA | CCACAGCAAA | CGCCTAAGAG | CAGGAAAAAT | 1653
| GTCTGCCAGG | AAAGTGTCCA | GTGTCCACAT | GGCCCCTGGC | GCTCTGAGTC | TTTGAGGAGT | 1713
| AATCGCAAGC | CTCGTTCAGC | TGCAGCAGAA | GGAAGGGCTT | AGCCAGGGTG | GGCGCTGGCG | 1773
| TCTGTGTTGA | AGGGAAACCA | AGCAGAAGCC | ACTGTAATGA | TATGTCACAA | TAAAACCCAT | 1833
| GAATGAAAAA | AAAAAAAAAA | AAAAAAAAAA | AAAAGAATTC | | | 1873

( 2 ) INFORMATION FOR SEQ ID NO:4:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | His | Val | Arg | Ser | Leu | Arg | Ala | Ala | Pro | His | Ser | Phe | Val | Ala |
| 1 | | | | 5 | | | | | 10 | | | | | 15 |
| Leu | Trp | Ala | Pro | Leu | Phe | Leu | Leu | Arg | Ser | Ala | Leu | Ala | Asp | Phe | Ser |
| | | | 20 | | | | | 25 | | | | | 30 | | |
| Leu | Asp | Asn | Glu | Val | His | Ser | Ser | Phe | Ile | His | Arg | Arg | Leu | Arg | Ser |
| | | | 35 | | | | | 40 | | | | | 45 | | |
| Gln | Glu | Arg | Arg | Glu | Met | Gln | Arg | Glu | Ile | Leu | Ser | Ile | Leu | Gly | Leu |
| | | | 50 | | | | | 55 | | | | | 60 | | |
| Pro | His | Arg | Pro | Arg | Pro | His | Leu | Gln | Gly | Lys | His | Asn | Ser | Ala | Pro |
| 65 | | | | | 70 | | | | | 75 | | | | | 80 |
| Met | Phe | Met | Leu | Asp | Leu | Tyr | Asn | Ala | Met | Ala | Val | Glu | Glu | Ser | Gly |
| | | | | 85 | | | | | 90 | | | | | 95 | |
| Pro | Asp | Gly | Gln | Gly | Phe | Ser | Tyr | Pro | Tyr | Lys | Ala | Val | Phe | Ser | Thr |
| | | | 100 | | | | | 105 | | | | | 110 | | |
| Gln | Gly | Pro | Pro | Leu | Ala | Ser | Leu | Gln | Asp | Ser | His | Phe | Leu | Thr | Asp |
| | | | 115 | | | | | 120 | | | | | 125 | | |
| Ala | Asp | Met | Val | Met | Ser | Phe | Val | Asn | Leu | Val | Glu | His | Asp | Lys | Glu |
| | | | 130 | | | | | 135 | | | | | 140 | | |
| Phe | Phe | His | Pro | Arg | Tyr | His | His | Arg | Glu | Phe | Arg | Phe | Asp | Leu | Ser |
| 145 | | | | | 150 | | | | | 155 | | | | | 160 |
| Lys | Ile | Pro | Glu | Gly | Glu | Arg | Val | Thr | Ala | Ala | Glu | Phe | Arg | Ile | Tyr |
| | | | | 165 | | | | | 170 | | | | | 175 | |
| Lys | Asp | Tyr | Ile | Arg | Glu | Arg | Phe | Asp | Asn | Glu | Thr | Phe | Gln | Ile | Thr |
| | | | 180 | | | | | 185 | | | | | 190 | | |
| Val | Tyr | Gln | Val | Leu | Gln | Glu | His | Ser | Gly | Arg | Glu | Ser | Asp | Leu | Phe |
| | | | 195 | | | | | 200 | | | | | 205 | | |
| Leu | Leu | Asp | Ser | Arg | Thr | Ile | Trp | Ala | Ser | Glu | Glu | Gly | Trp | Leu | Val |
| | 210 | | | | | 215 | | | | | 220 | | | | |
| Phe | Asp | Ile | Thr | Ala | Thr | Ser | Asn | His | Trp | Val | Val | Asn | Pro | Arg | His |
| 225 | | | | | 230 | | | | | 235 | | | | | 240 |
| Asn | Leu | Gly | Leu | Gln | Leu | Ser | Val | Glu | Thr | Leu | Asp | Gly | Gln | Ser | Ile |
| | | | | 245 | | | | | 250 | | | | | 255 | |
| Asn | Pro | Lys | Leu | Ala | Gly | Leu | Ile | Gly | Arg | His | Gly | Pro | Gln | Asn | Lys |
| | | | 260 | | | | | 265 | | | | | 270 | | |
| Gln | Pro | Phe | Met | Val | Ala | Phe | Phe | Lys | Ala | Thr | Glu | Val | His | Leu | Arg |
| | | | 275 | | | | | 280 | | | | | 285 | | |
| Ser | Ile | Arg | Ser | Thr | Gly | Gly | Lys | Gln | Arg | Ser | Gln | Asn | Arg | Ser | Lys |
| | 290 | | | | | 295 | | | | | 300 | | | | |
| Thr | Pro | Lys | Asn | Gln | Glu | Ala | Leu | Arg | Met | Ala | Ser | Val | Ala | Glu | Asn |
| 305 | | | | | 310 | | | | | 315 | | | | | 320 |
| Ser | Ser | Ser | Asp | Gln | Arg | Gln | Ala | Cys | Lys | Lys | His | Glu | Leu | Tyr | Val |
| | | | | 325 | | | | | 330 | | | | | 335 | |
| Ser | Phe | Arg | Asp | Leu | Gly | Trp | Gln | Asp | Trp | Ile | Ile | Ala | Pro | Glu | Gly |
| | | | 340 | | | | | 345 | | | | | 350 | | |
| Tyr | Ala | Ala | Tyr | Tyr | Cys | Glu | Gly | Glu | Cys | Ala | Phe | Pro | Leu | Asn | Ser |
| | | | 355 | | | | | 360 | | | | | 365 | | |
| Tyr | Met | Asn | Ala | Thr | Asn | His | Ala | Ile | Val | Gln | Thr | Leu | Val | His | Phe |
| | | | 370 | | | | | 375 | | | | | 380 | | |
| Ile | Asn | Pro | Asp | Thr | Val | Pro | Lys | Pro | Cys | Cys | Ala | Pro | Thr | Gln | Leu |
| 385 | | | | | 390 | | | | | 395 | | | | | 400 |
| Asn | Ala | Ile | Ser | Val | Leu | Tyr | Phe | Asp | Asp | Ser | Ser | Asn | Val | Ile | Leu |
| | | | | 405 | | | | | 410 | | | | | 415 | |
| Lys | Lys | Tyr | Arg | Asn | Met | Val | Val | Arg | Ala | Cys | Gly | Cys | His | | |
| | | | 420 | | | | | 425 | | | | | 430 | | |

( 2 ) INFORMATION FOR SEQ ID NO:5:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: HIPPOCAMPUS ( i x ) FEATURE:
        ( A ) NAME/KEY: CDS
        ( B ) LOCATION: 490..1696
        ( D ) OTHER INFORMATION: /function="OSTEOGENIC PROTEIN"
            / product= "hOP2-PP"
            / note= "hOP2 (cDNA)"

( x i ) SEQUENCE DESCRIPTION: SEQ ID NO:5:

```
GGCGCCGGCA  GAGCAGGAGT  GGCTGGAGGA  GCTGTGGTTG  GAGCAGGAGG  TGGCACGGCA           60

GGGCTGGAGG  GCTCCCTATG  AGTGGCGGAG  ACGGCCCAGG  AGGCGCTGGA  GCAACAGCTC          120

CCACACCGCA  CCAAGCGGTG  GCTGCAGGAG  CTCGCCCATC  GCCCCTGCGC  TGCTCGGACC          180

GCGGCCACAG  CCGGACTGGC  GGGTACGGCG  GCGACAGAGG  CATTGGCCGA  GAGTCCCAGT          240

CCGCAGAGTA  GCCCCGGCCT  CGAGGCGGTG  GCGTCCCGGT  CCTCTCCGTC  CAGGAGCCAG          300

GACAGGTGTC  GCGCGGCGGG  GCTCCAGGGA  CCGCGCCTGA  GGCCGGCTGC  CCGCCCGTCC          360

CGCCCCGCCC  CGCCGCCCGC  CGCCCGCCGA  GCCCAGCCTC  CTTGCCGTCG  GGGCGTCCCC          420

AGGCCCTGGG  TCGGCCGCGG  AGCCGATGCG  CGCCCGCTGA  GCGCCCCAGC  TGAGCGCCCC          480
```

```
CGGCCTGCC  ATG ACC GCG CTC CCC GGC CCG CTC TGG CTC CTG GGC CTG                  528
           Met Thr Ala Leu Pro Gly Pro Leu Trp Leu Leu Gly Leu
             1               5                          10

GCG CTA TGC GCG CTG GGC GGG GGC GGC CCC GGC CTG CGA CCC CCG CCC                 576
Ala Leu Cys Ala Leu Gly Gly Gly Gly Pro Gly Leu Arg Pro Pro Pro
         15                  20                  25

GGC TGT CCC CAG CGA CGT CTG GGC GCG CGC GAG CGC CGG GAC GTG CAG                 624
Gly Cys Pro Gln Arg Arg Leu Gly Ala Arg Glu Arg Arg Asp Val Gln
     30                  35                  40                  45

CGC GAG ATC CTG GCG GTG CTC GGG CTG CCT GGG CGG CCC CGG CCC CGC                 672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG                 720
Ala Pro Pro Ala Ala Ser Arg Leu Pro Ala Ser Ala Pro Leu Phe Met
                 65                  70                  75

CTG GAC CTG TAC CAC GCC ATG GCC GGC GAC GAC GAC GAG GAC GGC GCG                 768
Leu Asp Leu Tyr His Ala Met Ala Gly Asp Asp Asp Glu Asp Gly Ala
             80                  85                  90

CCC GCG GAG CGG CGC CTG GGC CGC GCC GAC CTG GTC ATG AGC TTC GTT                 816
Pro Ala Glu Arg Arg Leu Gly Arg Ala Asp Leu Val Met Ser Phe Val
         95                 100                 105

AAC ATG GTG GAG CGA GAC CGT GCC CTG GGC CAC CAG GAG CCC CAT TGG                 864
Asn Met Val Glu Arg Asp Arg Ala Leu Gly His Gln Glu Pro His Trp
110             115                 120                 125

AAG GAG TTC CGC TTT GAC CTG ACC CAG ATC CCG GCT GGG GAG GCG GTC                 912
Lys Glu Phe Arg Phe Asp Leu Thr Gln Ile Pro Ala Gly Glu Ala Val
             130                 135                 140

ACA GCT GCG GAG TTC CGG ATT TAC AAG GTG CCC AGC ATC CAC CTG CTC                 960
Thr Ala Ala Glu Phe Arg Ile Tyr Lys Val Pro Ser Ile His Leu Leu
                 145                 150                 155
```

| | | | | | | | | | | | | | | | | |
|---|---|---|---|---|---|---|---|---|---|---|---|---|---|---|---|---|
| AAC | AGG | ACC | CTC | CAC | GTC | AGC | ATG | TTC | CAG | GTG | GTC | CAG | GAG | CAG | TCC | 1008 |
| Asn | Arg | Thr | Leu | His | Val | Ser | Met | Phe | Gln | Val | Val | Gln | Glu | Gln | Ser | |
| | | 160 | | | | | 165 | | | | | 170 | | | | |
| AAC | AGG | GAG | TCT | GAC | TTG | TTC | TTT | TTG | GAT | CTT | CAG | ACG | CTC | CGA | GCT | 1056 |
| Asn | Arg | Glu | Ser | Asp | Leu | Phe | Phe | Leu | Asp | Leu | Gln | Thr | Leu | Arg | Ala | |
| | 175 | | | | | 180 | | | | | 185 | | | | | |
| GGA | GAC | GAG | GGC | TGG | CTG | GTG | CTG | GAT | GTC | ACA | GCA | GCC | AGT | GAC | TGC | 1104 |
| Gly | Asp | Glu | Gly | Trp | Leu | Val | Leu | Asp | Val | Thr | Ala | Ala | Ser | Asp | Cys | |
| 190 | | | | | 195 | | | | | 200 | | | | | 205 | |
| TGG | TTG | CTG | AAG | CGT | CAC | AAG | GAC | CTG | GGA | CTC | CGC | CTC | TAT | GTG | GAG | 1152 |
| Trp | Leu | Leu | Lys | Arg | His | Lys | Asp | Leu | Gly | Leu | Arg | Leu | Tyr | Val | Glu | |
| | | | | 210 | | | | | 215 | | | | | 220 | | |
| ACT | GAG | GAC | GGG | CAC | AGC | GTG | GAT | CCT | GGC | CTG | GCC | GGC | CTG | CTG | GGT | 1200 |
| Thr | Glu | Asp | Gly | His | Ser | Val | Asp | Pro | Gly | Leu | Ala | Gly | Leu | Leu | Gly | |
| | | | 225 | | | | | 230 | | | | | 235 | | | |
| CAA | CGG | GCC | CCA | CGC | TCC | CAA | CAG | CCT | TTC | GTG | GTC | ACT | TTC | TTC | AGG | 1248 |
| Gln | Arg | Ala | Pro | Arg | Ser | Gln | Gln | Pro | Phe | Val | Val | Thr | Phe | Phe | Arg | |
| | | 240 | | | | | 245 | | | | | 250 | | | | |
| GCC | AGT | CCG | AGT | CCC | ATC | CGC | ACC | CCT | CGG | GCA | GTG | AGG | CCA | CTG | AGG | 1296 |
| Ala | Ser | Pro | Ser | Pro | Ile | Arg | Thr | Pro | Arg | Ala | Val | Arg | Pro | Leu | Arg | |
| | 255 | | | | | 260 | | | | | 265 | | | | | |
| AGG | AGG | CAG | CCG | AAG | AAA | AGC | AAC | GAG | CTG | CCG | CAG | GCC | AAC | CGA | CTC | 1344 |
| Arg | Arg | Gln | Pro | Lys | Lys | Ser | Asn | Glu | Leu | Pro | Gln | Ala | Asn | Arg | Leu | |
| 270 | | | | | 275 | | | | | 280 | | | | | 285 | |
| CCA | GGG | ATC | TTT | GAT | GAC | GTC | CAC | GGC | TCC | CAC | GGC | CGG | CAG | GTC | TGC | 1392 |
| Pro | Gly | Ile | Phe | Asp | Asp | Val | His | Gly | Ser | His | Gly | Arg | Gln | Val | Cys | |
| | | | | 290 | | | | | 295 | | | | | 300 | | |
| CGT | CGG | CAC | GAG | CTC | TAC | GTC | AGC | TTC | CAG | GAC | CTC | GGC | TGG | CTG | GAC | 1440 |
| Arg | Arg | His | Glu | Leu | Tyr | Val | Ser | Phe | Gln | Asp | Leu | Gly | Trp | Leu | Asp | |
| | | | 305 | | | | | 310 | | | | | 315 | | | |
| TGG | GTC | ATC | GCT | CCC | CAA | GGC | TAC | TCG | GCC | TAT | TAC | TGT | GAG | GGG | GAG | 1488 |
| Trp | Val | Ile | Ala | Pro | Gln | Gly | Tyr | Ser | Ala | Tyr | Tyr | Cys | Glu | Gly | Glu | |
| | | 320 | | | | | 325 | | | | | 330 | | | | |
| TGC | TCC | TTC | CCA | CTG | GAC | TCC | TGC | ATG | AAT | GCC | ACC | AAC | CAC | GCC | ATC | 1536 |
| Cys | Ser | Phe | Pro | Leu | Asp | Ser | Cys | Met | Asn | Ala | Thr | Asn | His | Ala | Ile | |
| | 335 | | | | | 340 | | | | | 345 | | | | | |
| CTG | CAG | TCC | CTG | GTG | CAC | CTG | ATG | AAG | CCA | AAC | GCA | GTC | CCC | AAG | GCG | 1584 |
| Leu | Gln | Ser | Leu | Val | His | Leu | Met | Lys | Pro | Asn | Ala | Val | Pro | Lys | Ala | |
| 350 | | | | | 355 | | | | | 360 | | | | | 365 | |
| TGC | TGT | GCA | CCC | ACC | AAG | CTG | AGC | GCC | ACC | TCT | GTG | CTC | TAC | TAT | GAC | 1632 |
| Cys | Cys | Ala | Pro | Thr | Lys | Leu | Ser | Ala | Thr | Ser | Val | Leu | Tyr | Tyr | Asp | |
| | | | | 370 | | | | | 375 | | | | | 380 | | |
| AGC | AGC | AAC | AAC | GTC | ATC | CTG | CGC | AAA | GCC | CGC | AAC | ATG | GTG | GTC | AAG | 1680 |
| Ser | Ser | Asn | Asn | Val | Ile | Leu | Arg | Lys | Ala | Arg | Asn | Met | Val | Val | Lys | |
| | | | 385 | | | | | 390 | | | | | 395 | | | |
| GCC | TGC | GGC | TGC | CAC | T | GAGTCAGCCC | GCCCAGCCCT | ACTGCAG | | | | | | | | 1723 |
| Ala | Cys | Gly | Cys | His | | | | | | | | | | | | |
| | | 400 | | | | | | | | | | | | | | |

( 2 ) INFORMATION FOR SEQ ID NO:6:

( i ) SEQUENCE CHARACTERISTICS:
            ( A ) LENGTH: 402 amino acids
            ( B ) TYPE: amino acid
            ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Thr | Ala | Leu | Pro | Gly | Pro | Leu | Trp | Leu | Leu | Gly | Leu | Ala | Leu | Cys |
| 1 | | | | 5 | | | | | 10 | | | | | 15 | |

-continued

| Ala | Leu | Gly | Gly | Gly | Gly | Pro | Gly | Leu | Arg | Pro | Pro | Pro | Gly | Cys | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |
| Gln | Arg | Arg | Leu | Gly | Ala | Arg | Glu | Arg | Arg | Asp | Val | Gln | Arg | Glu | Ile |
|     |     |     | 35  |     |     |     |     | 40  |     |     |     |     | 45  |     |     |
| Leu | Ala | Val | Leu | Gly | Leu | Pro | Gly | Arg | Pro | Arg | Pro | Arg | Ala | Pro | Pro |
|     |     |     | 50  |     |     |     |     | 55  |     |     |     |     | 60  |     |     |
| Ala | Ala | Ser | Arg | Leu | Pro | Ala | Ser | Ala | Pro | Leu | Phe | Met | Leu | Asp | Leu |
| 65  |     |     |     |     | 70  |     |     |     |     | 75  |     |     |     |     | 80  |
| Tyr | His | Ala | Met | Ala | Gly | Asp | Asp | Asp | Glu | Asp | Gly | Ala | Pro | Ala | Glu |
|     |     |     |     | 85  |     |     |     |     | 90  |     |     |     |     | 95  |     |
| Arg | Arg | Leu | Gly | Arg | Ala | Asp | Leu | Val | Met | Ser | Phe | Val | Asn | Met | Val |
|     |     |     |     | 100 |     |     |     |     | 105 |     |     |     |     | 110 |     |
| Glu | Arg | Asp | Arg | Ala | Leu | Gly | His | Gln | Glu | Pro | His | Trp | Lys | Glu | Phe |
|     |     |     | 115 |     |     |     |     | 120 |     |     |     |     | 125 |     |     |
| Arg | Phe | Asp | Leu | Thr | Gln | Ile | Pro | Ala | Gly | Glu | Ala | Val | Thr | Ala | Ala |
|     |     | 130 |     |     |     |     | 135 |     |     |     |     | 140 |     |     |     |
| Glu | Phe | Arg | Ile | Tyr | Lys | Val | Pro | Ser | Ile | His | Leu | Leu | Asn | Arg | Thr |
| 145 |     |     |     |     | 150 |     |     |     |     | 155 |     |     |     |     | 160 |
| Leu | His | Val | Ser | Met | Phe | Gln | Val | Val | Gln | Gln | Ser | Asn | Arg | Glu |     |
|     |     |     |     | 165 |     |     |     |     | 170 |     |     |     | 175 |     |     |
| Ser | Asp | Leu | Phe | Phe | Leu | Asp | Leu | Gln | Thr | Leu | Arg | Ala | Gly | Asp | Glu |
|     |     |     | 180 |     |     |     |     | 185 |     |     |     |     | 190 |     |     |
| Gly | Trp | Leu | Val | Leu | Asp | Val | Thr | Ala | Ala | Ser | Asp | Cys | Trp | Leu | Leu |
|     |     |     | 195 |     |     |     |     | 200 |     |     |     |     | 205 |     |     |
| Lys | Arg | His | Lys | Asp | Leu | Gly | Leu | Arg | Leu | Tyr | Val | Glu | Thr | Glu | Asp |
|     |     | 210 |     |     |     |     | 215 |     |     |     |     | 220 |     |     |     |
| Gly | His | Ser | Val | Asp | Pro | Gly | Leu | Ala | Gly | Leu | Leu | Gly | Gln | Arg | Ala |
| 225 |     |     |     |     | 230 |     |     |     |     | 235 |     |     |     |     | 240 |
| Pro | Arg | Ser | Gln | Gln | Pro | Phe | Val | Val | Thr | Phe | Phe | Arg | Ala | Ser | Pro |
|     |     |     |     | 245 |     |     |     |     | 250 |     |     |     |     | 255 |     |
| Ser | Pro | Ile | Arg | Thr | Pro | Arg | Ala | Val | Arg | Pro | Leu | Arg | Arg | Arg | Gln |
|     |     |     |     | 260 |     |     |     |     | 265 |     |     |     |     | 270 |     |
| Pro | Lys | Lys | Ser | Asn | Glu | Leu | Pro | Gln | Ala | Asn | Arg | Leu | Pro | Gly | Ile |
|     |     | 275 |     |     |     |     | 280 |     |     |     |     | 285 |     |     |     |
| Phe | Asp | Asp | Val | His | Gly | Ser | His | Gly | Arg | Gln | Val | Cys | Arg | Arg | His |
|     |     | 290 |     |     |     |     | 295 |     |     |     |     | 300 |     |     |     |
| Glu | Leu | Tyr | Val | Ser | Phe | Gln | Asp | Leu | Gly | Trp | Leu | Asp | Trp | Val | Ile |
| 305 |     |     |     |     | 310 |     |     |     |     | 315 |     |     |     |     | 320 |
| Ala | Pro | Gln | Gly | Tyr | Ser | Ala | Tyr | Tyr | Cys | Glu | Gly | Glu | Cys | Ser | Phe |
|     |     |     |     | 325 |     |     |     |     | 330 |     |     |     |     | 335 |     |
| Pro | Leu | Asp | Ser | Cys | Met | Asn | Ala | Thr | Asn | His | Ala | Ile | Leu | Gln | Ser |
|     |     |     | 340 |     |     |     |     | 345 |     |     |     |     | 350 |     |     |
| Leu | Val | His | Leu | Met | Lys | Pro | Asn | Ala | Val | Pro | Lys | Ala | Cys | Cys | Ala |
|     |     | 355 |     |     |     |     | 360 |     |     |     |     | 365 |     |     |     |
| Pro | Thr | Lys | Leu | Ser | Ala | Thr | Ser | Val | Leu | Tyr | Tyr | Asp | Ser | Ser | Asn |
|     | 370 |     |     |     |     | 375 |     |     |     |     | 380 |     |     |     |     |
| Asn | Val | Ile | Leu | Arg | Lys | Ala | Arg | Asn | Met | Val | Val | Lys | Ala | Cys | Gly |
| 385 |     |     |     |     | 390 |     |     |     |     | 395 |     |     |     |     | 400 |
| Cys | His |     |     |     |     |     |     |     |     |     |     |     |     |     |     |

( 2 ) INFORMATION FOR SEQ ID NO:7:

( i ) SEQUENCE CHARACTERISTICS:
        ( A ) LENGTH: 1926 base pairs
        ( B ) TYPE: nucleic acid ( C ) STRANDEDNESS: single
( D ) TOPOLOGY: linear ( v i ) ORIGINAL SOURCE:
  ( A ) ORGANISM: MURIDAE
  ( F ) TISSUE TYPE: EMBRYO ( i x ) FEATURE:
  ( A ) NAME/KEY: CDS
  ( B ) LOCATION: 93..1289
  ( D ) OTHER INFORMATION: /function="OSTEOGENIC PROTEIN"
       / product= "mOP2-PP"
       / note= "mOP2 cDNA"

( x i ) SEQUENCE DESCRIPTION: SEQ ID NO:7:

```
GCCAGGCACA  GGTGCGCCGT  CTGGTCCTCC  CCGTCTGGCG  TCAGCCGAGC  CCGACCAGCT         60

ACCAGTGGAT  GCGCGCCGGC  TGAAAGTCCG  AG  ATG  GCT  ATG  CGT  CCC  GGG  CCA     113
                                        Met Ala Met Arg Pro Gly Pro
                                         1                    5

CTC  TGG  CTA  TTG  GGC  CTT  GCT  CTG  TGC  GCG  CTG  GGA  GGC  GGC  CAC  GGT    161
Leu  Trp  Leu  Leu  Gly  Leu  Ala  Leu  Cys  Ala  Leu  Gly  Gly  Gly  His  Gly
               10                   15                        20

CCG  CGT  CCC  CCG  CAC  ACC  TGT  CCC  CAG  CGT  CGC  CTG  GGA  GCG  CGC  GAG    209
Pro  Arg  Pro  Pro  His  Thr  Cys  Pro  Gln  Arg  Arg  Leu  Gly  Ala  Arg  Glu
          25                        30                        35

CGC  CGC  GAC  ATG  CAG  CGT  GAA  ATC  CTG  GCG  GTG  CTC  GGG  CTA  CCG  GGA    257
Arg  Arg  Asp  Met  Gln  Arg  Glu  Ile  Leu  Ala  Val  Leu  Gly  Leu  Pro  Gly
40                        45                        50                       55

CGG  CCC  CGA  CCC  CGT  GCA  CAA  CCC  GCC  GCT  GCC  CGG  CAG  CCA  GCG  TCC    305
Arg  Pro  Arg  Pro  Arg  Ala  Gln  Pro  Ala  Ala  Ala  Arg  Gln  Pro  Ala  Ser
                    60                        65                        70

GCG  CCC  CTC  TTC  ATG  TTG  GAC  CTA  TAC  CAC  GCC  ATG  ACC  GAT  GAC  GAC    353
Ala  Pro  Leu  Phe  Met  Leu  Asp  Leu  Tyr  His  Ala  Met  Thr  Asp  Asp  Asp
               75                        80                        85

GAC  GGC  GGG  CCA  CCA  CAG  GCT  CAC  TTA  GGC  CGT  GCC  GAC  CTG  GTC  ATG    401
Asp  Gly  Gly  Pro  Pro  Gln  Ala  His  Leu  Gly  Arg  Ala  Asp  Leu  Val  Met
          90                        95                       100

AGC  TTC  GTC  AAC  ATG  GTG  GAA  CGC  GAC  CGT  ACC  CTG  GGC  TAC  CAG  GAG    449
Ser  Phe  Val  Asn  Met  Val  Glu  Arg  Asp  Arg  Thr  Leu  Gly  Tyr  Gln  Glu
     105                      110                       115

CCA  CAC  TGG  AAG  GAA  TTC  CAC  TTT  GAC  CTA  ACC  CAG  ATC  CCT  GCT  GGG    497
Pro  His  Trp  Lys  Glu  Phe  His  Phe  Asp  Leu  Thr  Gln  Ile  Pro  Ala  Gly
120                      125                       130                      135

GAG  GCT  GTC  ACA  GCT  GCT  GAG  TTC  CGG  ATC  TAC  AAA  GAA  CCC  AGC  ACC    545
Glu  Ala  Val  Thr  Ala  Ala  Glu  Phe  Arg  Ile  Tyr  Lys  Glu  Pro  Ser  Thr
               140                      145                       150

CAC  CCG  CTC  AAC  ACA  ACC  CTC  CAC  ATC  AGC  ATG  TTC  GAA  GTG  GTC  CAA    593
His  Pro  Leu  Asn  Thr  Thr  Leu  His  Ile  Ser  Met  Phe  Glu  Val  Val  Gln
          155                      160                       165

GAG  CAC  TCC  AAC  AGG  GAG  TCT  GAC  TTG  TTC  TTT  TTG  GAT  CTT  CAG  ACG    641
Glu  His  Ser  Asn  Arg  Glu  Ser  Asp  Leu  Phe  Phe  Leu  Asp  Leu  Gln  Thr
               170                      175                       180

CTC  CGA  TCT  GGG  GAC  GAG  GGC  TGG  CTG  GTG  CTG  GAC  ATC  ACA  GCA  GCC    689
Leu  Arg  Ser  Gly  Asp  Glu  Gly  Trp  Leu  Val  Leu  Asp  Ile  Thr  Ala  Ala
     185                      190                       195

AGT  GAC  CGA  TGG  CTG  CTG  AAC  CAT  CAC  AAG  GAC  CTG  GGA  CTC  CGC  CTC    737
Ser  Asp  Arg  Trp  Leu  Leu  Asn  His  His  Lys  Asp  Leu  Gly  Leu  Arg  Leu
200                      205                       210                      215

TAT  GTG  GAA  ACC  GCG  GAT  GGG  CAC  AGC  ATG  GAT  CCT  GGC  CTG  GCT  GGT    785
Tyr  Val  Glu  Thr  Ala  Asp  Gly  His  Ser  Met  Asp  Pro  Gly  Leu  Ala  Gly
               220                      225                       230

CTG  CTT  GGA  CGA  CAA  GCA  CCA  CGC  TCC  AGA  CAG  CCT  TTC  ATG  GTA  ACC    833
Leu  Leu  Gly  Arg  Gln  Ala  Pro  Arg  Ser  Arg  Gln  Pro  Phe  Met  Val  Thr
```

```
                        235                         240                           245
TTC  TTC  AGG  GCC  AGC  CAG  AGT  CCT  GTG  CGG  GCC  CCT  CGG  GCA  GCG  AGA        881
Phe  Phe  Arg  Ala  Ser  Gln  Ser  Pro  Val  Arg  Ala  Pro  Arg  Ala  Ala  Arg
          250                      255                     260

CCA  CTG  AAG  AGG  AGG  CAG  CCA  AAG  AAA  ACG  AAC  GAG  CTT  CCG  CAC  CCC        929
Pro  Leu  Lys  Arg  Arg  Gln  Pro  Lys  Lys  Thr  Asn  Glu  Leu  Pro  His  Pro
          265                      270                     275

AAC  AAA  CTC  CCA  GGG  ATC  TTT  GAT  GAT  GGC  CAC  GGT  TCC  CGC  GGC  AGA        977
Asn  Lys  Leu  Pro  Gly  Ile  Phe  Asp  Asp  Gly  His  Gly  Ser  Arg  Gly  Arg
280                      285                     290                          295

GAG  GTT  TGC  CGC  AGG  CAT  GAG  CTC  TAC  GTC  AGC  TTC  CGT  GAC  CTT  GGC       1025
Glu  Val  Cys  Arg  Arg  His  Glu  Leu  Tyr  Val  Ser  Phe  Arg  Asp  Leu  Gly
                         300                     305                     310

TGG  CTG  GAC  TGG  GTC  ATC  GCC  CCC  CAG  GGC  TAC  TCT  GCC  TAT  TAC  TGT       1073
Trp  Leu  Asp  Trp  Val  Ile  Ala  Pro  Gln  Gly  Tyr  Ser  Ala  Tyr  Tyr  Cys
               315                      320                     325

GAG  GGG  GAG  TGT  GCT  TTC  CCA  CTG  GAC  TCC  TGT  ATG  AAC  GCC  ACC  AAC       1121
Glu  Gly  Glu  Cys  Ala  Phe  Pro  Leu  Asp  Ser  Cys  Met  Asn  Ala  Thr  Asn
          330                      335                     340

CAT  GCC  ATC  TTG  CAG  TCT  CTG  GTG  CAC  CTG  ATG  AAG  CCA  GAT  GTT  GTC       1169
His  Ala  Ile  Leu  Gln  Ser  Leu  Val  His  Leu  Met  Lys  Pro  Asp  Val  Val
     345                      350                     355

CCC  AAG  GCA  TGC  TGT  GCA  CCC  ACC  AAA  CTG  AGT  GCC  ACC  TCT  GTG  CTG       1217
Pro  Lys  Ala  Cys  Cys  Ala  Pro  Thr  Lys  Leu  Ser  Ala  Thr  Ser  Val  Leu
360                      365                     370                          375

TAC  TAT  GAC  AGC  AGC  AAC  AAT  GTC  ATC  CTG  CGT  AAA  CAC  CGT  AAC  ATG       1265
Tyr  Tyr  Asp  Ser  Ser  Asn  Asn  Val  Ile  Leu  Arg  Lys  His  Arg  Asn  Met
                    380                      385                     390

GTG  GTC  AAG  GCC  TGT  GGC  TGC  CAC  TGAGGCCCCG  CCCAGCATCC  TGCTTCTACT           1319
Val  Val  Lys  Ala  Cys  Gly  Cys  His
               395

ACCTTACCAT  CTGGCCGGGC  CCCTCTCCAG  AGGCAGAAAC  CCTTCTATGT  TATCATAGCT              1379

CAGACAGGGG  CAATGGGAGG  CCCTTCACTT  CCCCTGGCCA  CTTCCTGCTA  AAATTCTGGT              1439

CTTTCCAGT  TCCTCTGTCC  TTCATGGGGT  TTCGGGGCTA  TCACCCCGCC  CTCTCCATCC               1499

TCCTACCCCA  AGCATAGACT  GAATGCACAC  AGCATCCAG   AGCTATGCTA  ACTGAGAGGT              1559

CTGGGGTCAG  CACTGAAGGC  CCACATGAGG  AAGACTGATC  CTTGGCCATC  CTCAGCCCAC              1619

AATGGCAAAT  TCTGGATGGT  CTAAGAAGGC  CCTGGAATTC  TAAACTAGAT  GATCTGGGCT              1679

CTCTGCACCA  TTCATTGTGG  CAGTTGGGAC  ATTTTTAGGT  ATAACAGACA  CATACACTTA              1739

GATCAATGCA  TCGCTGTACT  CCTTGAAATC  AGAGCTAGCT  TGTTAGAAAA  AGAATCAGAG              1799

CCAGGTATAG  CGGTGCATGT  CATTAATCCC  AGCGCTAAAG  AGACAGAGAC  AGGAGAATCT              1859

CTGTGAGTTC  AAGGCCACAT  AGAAAGAGCC  TGTCTCGGGA  GCAGGAAAAA  AAAAAAAAAC              1919

GGAATTC                                                                             1926
```

( 2 ) INFORMATION FOR SEQ ID NO:8:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ala  Met  Arg  Pro  Gly  Pro  Leu  Trp  Leu  Leu  Gly  Leu  Ala  Leu  Cys
 1              5                        10                            15

Ala  Leu  Gly  Gly  Gly  His  Gly  Pro  Arg  Pro  Pro  His  Thr  Cys  Pro  Gln
```

```
                        20                         25                          30
Arg  Arg  Leu  Gly  Ala  Arg  Glu  Arg  Asp  Met  Gln  Arg  Glu  Ile  Leu
               35                       40                      45
Ala  Val  Leu  Gly  Leu  Pro  Gly  Arg  Pro  Arg  Pro  Arg  Ala  Gln  Pro  Ala
          50                       55                      60
Ala  Ala  Arg  Gln  Pro  Ala  Ser  Ala  Pro  Leu  Phe  Met  Leu  Asp  Leu  Tyr
 65                       70                      75                            80
His  Ala  Met  Thr  Asp  Asp  Asp  Gly  Gly  Pro  Pro  Gln  Ala  His  Leu
                         85                      90                      95
Gly  Arg  Ala  Asp  Leu  Val  Met  Ser  Phe  Val  Asn  Met  Val  Glu  Arg  Asp
               100                      105                     110
Arg  Thr  Leu  Gly  Tyr  Gln  Glu  Pro  His  Trp  Lys  Glu  Phe  His  Phe  Asp
               115                      120                     125
Leu  Thr  Gln  Ile  Pro  Ala  Gly  Glu  Ala  Val  Thr  Ala  Ala  Glu  Phe  Arg
               130                      135                     140
Ile  Tyr  Lys  Glu  Pro  Ser  Thr  His  Pro  Leu  Asn  Thr  Thr  Leu  His  Ile
145                                150                     155                 160
Ser  Met  Phe  Glu  Val  Val  Gln  Glu  His  Ser  Asn  Arg  Glu  Ser  Asp  Leu
                         165                     170                     175
Phe  Phe  Leu  Asp  Leu  Gln  Thr  Leu  Arg  Ser  Gly  Asp  Glu  Gly  Trp  Leu
               180                      185                     190
Val  Leu  Asp  Ile  Thr  Ala  Ala  Ser  Asp  Arg  Trp  Leu  Leu  Asn  His  His
               195                      200                     205
Lys  Asp  Leu  Gly  Leu  Arg  Leu  Tyr  Val  Glu  Thr  Ala  Asp  Gly  His  Ser
          210                      215                     220
Met  Asp  Pro  Gly  Leu  Ala  Gly  Leu  Leu  Gly  Arg  Gln  Ala  Pro  Arg  Ser
225                           230                      235                    240
Arg  Gln  Pro  Phe  Met  Val  Thr  Phe  Phe  Arg  Ala  Ser  Gln  Ser  Pro  Val
                    245                           250                    255
Arg  Ala  Pro  Arg  Ala  Ala  Arg  Pro  Leu  Lys  Arg  Arg  Gln  Pro  Lys  Lys
               260                           265                    270
Thr  Asn  Glu  Leu  Pro  His  Pro  Asn  Lys  Leu  Pro  Gly  Ile  Phe  Asp  Asp
          275                           280                    285
Gly  His  Gly  Ser  Arg  Gly  Arg  Glu  Val  Cys  Arg  Arg  His  Glu  Leu  Tyr
     290                           295                    300
Val  Ser  Phe  Arg  Asp  Leu  Gly  Trp  Leu  Asp  Trp  Val  Ile  Ala  Pro  Gln
305                           310                      315                    320
Gly  Tyr  Ser  Ala  Tyr  Tyr  Cys  Glu  Gly  Glu  Cys  Ala  Phe  Pro  Leu  Asp
                    325                           330                    335
Ser  Cys  Met  Asn  Ala  Thr  Asn  His  Ala  Ile  Leu  Gln  Ser  Leu  Val  His
               340                           345                    350
Leu  Met  Lys  Pro  Asp  Val  Val  Pro  Lys  Ala  Cys  Cys  Ala  Pro  Thr  Lys
          355                           360                    365
Leu  Ser  Ala  Thr  Ser  Val  Leu  Tyr  Tyr  Asp  Ser  Ser  Asn  Asn  Val  Ile
     370                           375                    380
Leu  Arg  Lys  His  Arg  Asn  Met  Val  Val  Lys  Ala  Cys  Gly  Cys  His
385                           390                    395
```

( 2 ) INFORMATION FOR SEQ ID NO:9:

( i ) SEQUENCE CHARACTERISTICS:
        ( A ) LENGTH: 399 amino acids
        ( B ) TYPE: amino acid
        ( C ) STRANDEDNESS: single
        ( D ) TOPOLOGY: linear ( i i ) MOLECULE TYPE: protein ( i x ) FEATURE:
    ( A ) NAME/KEY: Protein
    ( B ) LOCATION: 1..399
    ( D ) OTHER INFORMATION: /note= "PRE-PRO-OP3 (MOUSE)"

( x i ) SEQUENCE DESCRIPTION: SEQ ID NO:9:

```
Met Ala Ala Arg Pro Gly Leu Leu Trp Leu Leu Gly Leu Ala Leu Cys
 1               5                  10                  15

Val Leu Gly Gly Gly His Leu Ser His Pro Pro His Val Phe Pro Gln
            20                  25                  30

Arg Arg Leu Gly Val Arg Glu Pro Arg Asp Met Gln Arg Glu Ile Arg
        35                  40                  45

Glu Val Leu Gly Leu Ala Gly Arg Pro Arg Ser Arg Ala Pro Val Gly
    50                  55                  60

Ala Ala Gln Gln Pro Ala Ser Ala Pro Leu Phe Met Leu Asp Leu Tyr
65                  70                  75                  80

Arg Ala Met Thr Asp Asp Ser Gly Gly Thr Pro Gln Pro His Leu
            85                  90                  95

Asp Arg Ala Asp Leu Ile Met Ser Phe Val Asn Ile Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
    130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
            165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Glu Asp Gly His Ser
210                 215                 220

Ile Asp Pro Gly Leu Ala Gly Leu Leu Gly Arg Gln Ala Pro Arg Ser
225                 230                 235                 240

Arg Gln Pro Phe Met Val Gly Phe Phe Arg Ala Asn Gln Ser Pro Val
            245                 250                 255

Arg Ala Pro Arg Thr Ala Arg Pro Leu Lys Lys Lys Gln Leu Asn Gln
            260                 265                 270

Ile Asn Gln Leu Pro His Ser Asn Lys His Leu Gly Ile Leu Asp Asp
        275                 280                 285

Gly His Gly Ser His Gly Arg Glu Val Cys Arg Arg His Glu Leu Tyr
    290                 295                 300

Val Ser Phe Arg Asp Leu Gly Trp Leu Asp Ser Val Ile Ala Pro Gln
305                 310                 315                 320

Gly Tyr Ser Ala Tyr Tyr Cys Ala Gly Glu Cys Ile Tyr Pro Leu Asn
                325                 330                 335

Ser Cys Met Asn Ser Thr Asn His Ala Thr Met Gln Ala Leu Val His
            340                 345                 350

Leu Met Lys Pro Asp Ile Ile Pro Lys Val Cys Cys Val Pro Thr Glu
        355                 360                 365

Leu Ser Ala Ile Ser Leu Leu Tyr Tyr Asp Arg Asn Asn Val Ile
        370                 375                 380
```

```
              Leu  Arg  Arg  Glu  Arg  Asn  Met  Val  Val  Gln  Ala  Cys  Gly  Cys  His
              385                      390                      395
```

(2) INFORMATION FOR SEQ ID NO:10:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..396
        (D) OTHER INFORMATION: /note= "PRE-PRO-BMP2 (HUMAN)"

(x) PUBLICATION INFORMATION:
        (A) AUTHORS: WOZNEY,
        (C) JOURNAL: SCIENCE
        (D) VOLUME: 242
        (F) PAGES: 1528-1534
        (G) DATE: 1988

(xi) SEQUENCE DESCRIPTION: SEQ ID NO:10:

```
Met  Val  Ala  Gly  Thr  Arg  Cys  Leu  Leu  Ala  Leu  Leu  Leu  Pro  Gln  Val
1                   5                        10                       15

Leu  Leu  Gly  Gly  Ala  Ala  Gly  Leu  Val  Pro  Glu  Leu  Gly  Arg  Arg  Lys
               20                       25                       30

Phe  Ala  Ala  Ala  Ser  Ser  Gly  Arg  Pro  Ser  Ser  Gln  Pro  Ser  Asp  Glu
               35                       40                       45

Val  Leu  Ser  Glu  Phe  Glu  Leu  Arg  Leu  Leu  Ser  Met  Phe  Gly  Leu  Lys
     50                       55                       60

Gln  Arg  Pro  Thr  Pro  Ser  Arg  Asp  Ala  Val  Val  Pro  Pro  Tyr  Met  Leu
65                       70                       75                       80

Asp  Leu  Tyr  Arg  Arg  His  Ser  Gly  Gln  Pro  Gly  Ser  Pro  Ala  Pro  Asp
               85                       90                       95

His  Arg  Leu  Glu  Arg  Ala  Ala  Ser  Arg  Ala  Asn  Thr  Val  Arg  Ser  Phe
               100                      105                      110

His  His  Glu  Glu  Ser  Leu  Glu  Glu  Leu  Pro  Glu  Thr  Ser  Gly  Lys  Thr
               115                      120                      125

Thr  Arg  Arg  Phe  Phe  Phe  Asn  Leu  Ser  Ser  Ile  Pro  Thr  Glu  Glu  Phe
     130                      135                      140

Ile  Thr  Ser  Ala  Glu  Leu  Gln  Val  Phe  Arg  Glu  Gln  Met  Gln  Asp  Ala
145                      150                      155                      160

Leu  Gly  Asn  Asn  Ser  Ser  Phe  His  His  Arg  Ile  Asn  Ile  Tyr  Glu  Ile
               165                      170                      175

Ile  Lys  Pro  Ala  Thr  Ala  Asn  Ser  Lys  Phe  Pro  Val  Thr  Arg  Leu  Leu
               180                      185                      190

Asp  Thr  Arg  Leu  Val  Asn  Gln  Asn  Ala  Ser  Arg  Trp  Glu  Ser  Phe  Asp
     195                      200                      205

Val  Thr  Pro  Ala  Val  Met  Arg  Trp  Thr  Ala  Gln  Gly  His  Ala  Asn  His
     210                      215                      220

Gly  Phe  Val  Val  Glu  Val  Ala  His  Leu  Glu  Glu  Lys  Gln  Gly  Val  Ser
225                      230                      235                      240

Lys  Arg  His  Val  Arg  Ile  Ser  Arg  Ser  Leu  His  Gln  Asp  Glu  His  Ser
               245                      250                      255

Trp  Ser  Gln  Ile  Arg  Pro  Leu  Leu  Val  Thr  Phe  Gly  His  Asp  Gly  Lys
               260                      265                      270
```

-continued

```
Gly His Pro Leu His Lys Arg Glu Lys Arg Gln Ala Lys His Lys Gln
    275                 280                 285
Arg Lys Arg Leu Lys Ser Ser Cys Lys Arg His Pro Leu Tyr Val Asp
    290                 295                 300
Phe Ser Asp Val Gly Trp Asn Asp Trp Ile Val Ala Pro Pro Gly Tyr
305                     310                 315                 320
His Ala Phe Tyr Cys His Gly Glu Cys Pro Phe Pro Leu Ala Asp His
                325                 330                 335
Leu Asn Ser Thr Asn His Ala Ile Val Gln Thr Leu Val Asn Ser Val
            340                 345                 350
Asn Ser Lys Ile Pro Lys Ala Cys Cys Val Pro Thr Glu Leu Ser Ala
        355                 360                 365
Ile Ser Met Leu Tyr Leu Asp Glu Asn Glu Lys Val Val Leu Lys Asn
    370                 375                 380
Tyr Gln Asp Met Val Val Glu Gly Cys Gly Cys Arg
385                 390                 395
```

( 2 ) INFORMATION FOR SEQ ID NO:11:

( i ) SEQUENCE CHARACTERISTICS:
        ( A ) LENGTH: 408 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..408
        ( D ) OTHER INFORMATION: /note= "PRE-PRO-BMP4 (HUMAN)"

( x i ) SEQUENCE DESCRIPTION: SEQ ID NO:11:

```
Met Ile Pro Gly Asn Arg Met Leu Met Val Val Leu Leu Cys Gln Val
1               5                   10                  15
Leu Leu Gly Gly Ala Ser His Ala Ser Leu Ile Pro Glu Thr Gly Lys
            20                  25                  30
Lys Lys Val Ala Glu Ile Gln Gly His Ala Gly Gly Arg Arg Ser Gly
        35                  40                  45
Gln Ser His Glu Leu Leu Arg Asp Phe Glu Ala Thr Leu Leu Gln Met
    50                  55                  60
Phe Gly Leu Arg Arg Arg Pro Gln Pro Ser Lys Ser Ala Val Ile Pro
65                  70                  75                  80
Asp Tyr Met Arg Asp Leu Tyr Arg Leu Gln Ser Gly Glu Glu Glu Glu
                85                  90                  95
Glu Gln Ile His Ser Thr Gly Leu Glu Tyr Pro Glu Arg Pro Ala Ser
            100                 105                 110
Arg Ala Asn Thr Val Arg Ser Phe His His Glu Glu His Leu Glu Asn
        115                 120                 125
Ile Pro Gly Thr Ser Glu Asn Ser Ala Phe Arg Phe Leu Phe Asn Leu
    130                 135                 140
Ser Ser Ile Pro Glu Asn Glu Val Ile Ser Ser Ala Glu Leu Arg Leu
145                 150                 155                 160
Phe Arg Glu Gln Val Asp Gln Gly Pro Asp Trp Glu Arg Gly Phe His
                165                 170                 175
Arg Ile Asn Ile Tyr Glu Val Met Lys Pro Pro Ala Glu Val Val Pro
            180                 185                 190
Gly His Leu Ile Thr Arg Leu Leu Asp Thr Arg Leu Val His His Asn
        195                 200                 205
```

```
Val  Thr  Arg  Trp  Glu  Thr  Phe  Asp  Val  Ser  Pro  Ala  Val  Leu  Arg  Trp
     210                      215                 220

Thr  Arg  Glu  Lys  Gln  Pro  Asn  Tyr  Gly  Leu  Ala  Ile  Glu  Val  Thr  His
225                      230                      235                      240

Leu  His  Gln  Thr  Arg  Thr  His  Gln  Gly  Gln  His  Val  Arg  Ile  Ser  Arg
                    245                      250                      255

Ser  Leu  Pro  Gln  Gly  Ser  Gly  Asn  Trp  Ala  Gln  Leu  Arg  Pro  Leu  Leu
               260                      265                      270

Val  Thr  Phe  Gly  His  Asp  Gly  Arg  Gly  His  Ala  Leu  Thr  Arg  Arg  Arg
          275                      280                      285

Arg  Ala  Lys  Arg  Ser  Pro  Lys  His  His  Ser  Gln  Arg  Ala  Arg  Lys  Lys
     290                      295                      300

Asn  Lys  Asn  Cys  Arg  Arg  His  Ser  Leu  Tyr  Val  Asp  Phe  Ser  Asp  Val
305                      310                      315                      320

Gly  Trp  Asn  Asp  Trp  Ile  Val  Ala  Pro  Pro  Gly  Tyr  Gln  Ala  Phe  Tyr
                    325                      330                      335

Cys  His  Gly  Asp  Cys  Pro  Phe  Pro  Leu  Ala  Asp  His  Leu  Asn  Ser  Thr
               340                      345                      350

Asn  His  Ala  Ile  Val  Gln  Thr  Leu  Val  Asn  Ser  Val  Asn  Ser  Ser  Ile
          355                      360                      365

Pro  Lys  Ala  Cys  Cys  Val  Pro  Thr  Glu  Leu  Ser  Ala  Ile  Ser  Met  Leu
     370                      375                      380

Tyr  Leu  Asp  Glu  Tyr  Asp  Lys  Val  Val  Leu  Lys  Asn  Tyr  Gln  Glu  Met
385                      390                      395                      400

Val  Val  Glu  Gly  Cys  Gly  Cys  Arg
               405
```

( 2 ) INFORMATION FOR SEQ ID NO:12:

( i ) SEQUENCE CHARACTERISTICS:
        ( A ) LENGTH: 588 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..588
        ( D ) OTHER INFORMATION: /note= "PRE-PRO-DPP"

( x ) PUBLICATION INFORMATION:
        ( A ) AUTHORS: PADGETT,
        ( C ) JOURNAL: NATURE
        ( D ) VOLUME: 325
        ( F ) PAGES: 81-84
        ( G ) DATE: 1987

( x i ) SEQUENCE DESCRIPTION: SEQ ID NO:12:

```
Met  Arg  Ala  Trp  Leu  Leu  Leu  Leu  Ala  Val  Leu  Ala  Thr  Phe  Gln  Thr
1                   5                   10                      15

Ile  Val  Arg  Val  Ala  Ser  Thr  Glu  Asp  Ile  Ser  Gln  Arg  Phe  Ile  Ala
          20                      25                      30

Ala  Ile  Ala  Pro  Val  Ala  Ala  His  Ile  Pro  Leu  Ala  Ser  Ala  Ser  Gly
          35                      40                      45

Ser  Gly  Ser  Gly  Arg  Ser  Gly  Ser  Arg  Ser  Val  Gly  Ala  Ser  Thr  Ser
     50                      55                      60

Thr  Ala  Leu  Ala  Lys  Ala  Phe  Asn  Pro  Phe  Ser  Glu  Pro  Ala  Ser  Phe
65                      70                      75                      80
```

```
Ser  Asp  Ser  Asp  Lys  Ser  His  Arg  Ser  Lys  Thr  Asn  Lys  Lys  Pro  Ser
               85                  90                            95

Lys  Ser  Asp  Ala  Asn  Arg  Gln  Phe  Asn  Glu  Val  His  Lys  Pro  Arg  Thr
                    100                 105                      110

Asp  Gln  Leu  Glu  Asn  Ser  Lys  Asn  Lys  Ser  Lys  Gln  Leu  Val  Asn  Lys
               115                 120                      125

Pro  Asn  His  Asn  Lys  Met  Ala  Val  Lys  Glu  Gln  Arg  Ser  His  His  Lys
          130                 135                      140

Lys  Ser  His  His  Arg  Ser  His  Gln  Pro  Lys  Gln  Ala  Ser  Ala  Ser
145                      150                 155                           160

Thr  Glu  Ser  His  Gln  Ser  Ser  Ser  Ile  Glu  Ser  Ile  Phe  Val  Glu  Glu
                    165                      170                      175

Pro  Thr  Leu  Val  Leu  Asp  Arg  Glu  Val  Ala  Ser  Ile  Asn  Val  Pro  Ala
               180                 185                      190

Asn  Ala  Lys  Ala  Ile  Ile  Ala  Glu  Gln  Gly  Pro  Ser  Thr  Tyr  Ser  Lys
               195                 200                      205

Glu  Ala  Leu  Ile  Lys  Asp  Lys  Leu  Lys  Pro  Asp  Pro  Ser  Thr  Leu  Val
          210                 215                      220

Glu  Ile  Glu  Lys  Ser  Leu  Ser  Leu  Phe  Asn  Met  Lys  Arg  Pro  Pro
225                      230                 235                           240

Lys  Ile  Asp  Arg  Ser  Lys  Ile  Ile  Ile  Pro  Glu  Pro  Met  Lys  Lys  Leu
                    245                 250                      255

Tyr  Ala  Glu  Ile  Asn  Gly  His  Glu  Leu  Asp  Ser  Val  Asn  Ile  Pro  Lys
               260                 265                      270

Pro  Gly  Leu  Leu  Thr  Lys  Ser  Ala  Asn  Thr  Val  Arg  Ser  Phe  Thr  His
          275                 280                      285

Lys  Asp  Ser  Lys  Ile  Asp  Asp  Arg  Phe  Pro  His  His  Arg  Phe  Arg
290                      295                      300

Leu  His  Phe  Asp  Val  Lys  Ser  Ile  Pro  Ala  Asp  Glu  Lys  Leu  Lys  Ala
305                      310                 315                           320

Ala  Glu  Leu  Gln  Leu  Thr  Arg  Asp  Ala  Leu  Ser  Gln  Gln  Val  Val  Ala
                    325                      330                      335

Ser  Arg  Ser  Ser  Ala  Asn  Arg  Thr  Arg  Tyr  Gln  Val  Leu  Val  Tyr  Asp
                    340                      345                 350

Ile  Thr  Arg  Val  Gly  Val  Arg  Gly  Gln  Arg  Glu  Pro  Ser  Tyr  Leu  Leu
          355                      360                      365

Leu  Asp  Thr  Lys  Thr  Val  Arg  Leu  Asn  Ser  Thr  Asp  Thr  Val  Ser  Leu
          370                 375                      380

Asp  Val  Gln  Pro  Ala  Val  Asp  Arg  Trp  Leu  Ala  Ser  Pro  Gln  Arg  Asn
385                      390                      395                      400

Tyr  Gly  Leu  Leu  Val  Glu  Val  Arg  Thr  Val  Arg  Ser  Leu  Lys  Pro  Ala
                    405                      410                      415

Pro  His  His  His  Val  Arg  Leu  Arg  Arg  Ser  Ala  Asp  Glu  Ala  His  Glu
               420                      425                      430

Arg  Trp  Gln  His  Lys  Gln  Pro  Leu  Leu  Phe  Thr  Tyr  Thr  Asp  Asp  Gly
          435                      440                      445

Arg  His  Lys  Ala  Arg  Ser  Ile  Arg  Asp  Val  Ser  Gly  Gly  Glu  Gly  Gly
          450                 455                      460

Gly  Lys  Gly  Gly  Arg  Asn  Lys  Arg  His  Ala  Arg  Arg  Pro  Thr  Arg  Arg
465                      470                      475                      480

Lys  Asn  His  Asp  Asp  Thr  Cys  Arg  Arg  His  Ser  Leu  Tyr  Val  Asp  Phe
                    485                      490                      495

Ser  Asp  Val  Gly  Trp  Asp  Asp  Trp  Ile  Val  Ala  Pro  Leu  Gly  Tyr  Asp
               500                      505                      510
```

|     |     |     |     |     |     |     |     |     |     |     |     |     |     |     |
| --- | --- | --- | --- | --- | --- | --- | --- | --- | --- | --- | --- | --- | --- | --- |
| Ala | Tyr | Tyr<br>515 | Cys | His | Gly | Lys | Cys<br>520 | Pro | Phe | Pro | Leu | Ala<br>525 | Asp | His | Phe |
| Asn | Ser<br>530 | Thr | Asn | His | Ala<br>535 | Val | Val | Gln | Thr | Leu | Val<br>540 | Asn | Asn | Met | Asn |
| Pro<br>545 | Gly | Lys | Val | Pro | Lys<br>550 | Ala | Cys | Cys | Val | Pro<br>555 | Thr | Gln | Leu | Asp | Ser<br>560 |
| Val | Ala | Met | Leu | Tyr<br>565 | Leu | Asn | Asp | Gln | Ser<br>570 | Thr | Val | Val | Leu | Lys<br>575 | Asn |
| Tyr | Gln | Glu | Met<br>580 | Thr | Val | Val | Gly | Cys<br>585 | Gly | Cys | Arg |     |     |     |     |

( 2 ) INFORMATION FOR SEQ ID NO:13:

( i ) SEQUENCE CHARACTERISTICS:
       ( A ) LENGTH: 360 amino acids
       ( B ) TYPE: amino acid
       ( C ) STRANDEDNESS: single
       ( D ) TOPOLOGY: linear ( i i ) MOLECULE TYPE: protein ( i x ) FEATURE:
       ( A ) NAME/KEY: Protein
       ( B ) LOCATION: 1..360
       ( D ) OTHER INFORMATION: /note= "PRE-PRO-VG1"

( x ) PUBLICATION INFORMATION:
       ( A ) AUTHORS: WEEKS,
       ( C ) JOURNAL: CELL
       ( D ) VOLUME: 51
       ( F ) PAGES: 861-867
       ( G ) DATE: 1987

( x i ) SEQUENCE DESCRIPTION: SEQ ID NO:13:

|     |     |     |     |     |     |     |     |     |     |     |     |     |     |     |     |
| --- | --- | --- | --- | --- | --- | --- | --- | --- | --- | --- | --- | --- | --- | --- | --- |
| Met<br>1 | Val | Trp | Leu | Arg<br>5 | Leu | Trp | Ala | Phe | Leu<br>10 | His | Ile | Leu | Ala | Ile<br>15 | Val |
| Thr | Leu | Asp | Pro<br>20 | Glu | Leu | Lys | Arg<br>25 | Arg | Glu | Glu | Leu | Phe<br>30 | Leu | Arg | Ser |
| Leu | Gly | Phe<br>35 | Ser | Ser | Lys | Pro | Asn<br>40 | Pro | Val | Ser | Pro | Pro<br>45 | Pro | Val | Pro |
| Ser | Ile<br>50 | Leu | Trp | Arg | Ile | Phe<br>55 | Asn | Gln | Arg | Met | Gly<br>60 | Ser | Ser | Ile | Gln |
| Lys<br>65 | Lys | Lys | Pro | Asp | Leu<br>70 | Cys | Phe | Val | Glu | Glu<br>75 | Phe | Asn | Val | Pro | Gly<br>80 |
| Ser | Val | Ile | Arg | Val<br>85 | Phe | Pro | Asp | Gln | Gly<br>90 | Arg | Phe | Ile | Ile | Pro<br>95 | Tyr |
| Ser | Asp | Asp | Ile<br>100 | His | Pro | Thr | Gln | Cys<br>105 | Leu | Gly | Lys | Arg | Leu<br>110 | Phe | Phe |
| Asn | Ile | Ser<br>115 | Ala | Ile | Glu | Lys | Glu<br>120 | Glu | Arg | Val | Thr | Met<br>125 | Gly | Ser | Gly |
| Ile | Glu<br>130 | Val | Gln | Pro | Glu | His<br>135 | Leu | Leu | Arg | Lys | Gly<br>140 | Ile | Asp | Leu | Arg |
| Leu<br>145 | Tyr | Arg | Thr | Leu | Gln<br>150 | Ile | Thr | Leu | Lys | Gly<br>155 | Met | Gly | Arg | Ser | Lys<br>160 |
| Thr | Ser | Arg | Lys | Leu<br>165 | Leu | Val | Ala | Gln | Thr<br>170 | Phe | Arg | Leu | Leu | His<br>175 | Lys |
| Ser | Leu | Phe | Phe<br>180 | Asn | Leu | Thr | Glu | Ile<br>185 | Cys | Gln | Ser | Trp | Gln<br>190 | Asp | Pro |
| Leu | Lys | Asn<br>195 | Leu | Gly | Leu | Val | Leu<br>200 | Glu | Ile | Phe | Pro | Lys<br>205 | Lys | Glu | Ser |

```
Ser  Trp  Met  Ser  Thr  Ala  Asn  Asp  Glu  Cys  Lys  Asp  Ile  Gln  Thr  Phe
     210                 215                 220

Leu  Tyr  Thr  Ser  Leu  Leu  Thr  Val  Thr  Leu  Asn  Pro  Leu  Arg  Cys  Lys
225                      230                 235                           240

Arg  Pro  Arg  Arg  Lys  Arg  Ser  Tyr  Ser  Lys  Leu  Pro  Phe  Thr  Ala  Ser
               245                      250                           255

Asn  Ile  Cys  Lys  Lys  Arg  His  Leu  Tyr  Val  Glu  Phe  Lys  Asp  Val  Gly
               260                 265                      270

Trp  Gln  Asn  Trp  Val  Ile  Ala  Pro  Gln  Gly  Tyr  Met  Ala  Asn  Tyr  Cys
          275                 280                      285

Tyr  Gly  Glu  Cys  Pro  Tyr  Pro  Leu  Thr  Glu  Ile  Leu  Asn  Gly  Ser  Asn
     290                 295                      300

His  Ala  Ile  Leu  Gln  Thr  Leu  Val  His  Ser  Ile  Glu  Pro  Glu  Asp  Ile
305                      310                 315                           320

Pro  Leu  Pro  Cys  Cys  Val  Pro  Thr  Lys  Met  Ser  Pro  Ile  Ser  Met  Leu
               325                 330                      335

Phe  Tyr  Asp  Asn  Asn  Asp  Asn  Val  Val  Leu  Arg  His  Tyr  Glu  Asn  Met
          340                 345                      350

Ala  Val  Asp  Glu  Cys  Gly  Cys  Arg
          355                 360
```

(2) INFORMATION FOR SEQ ID NO:14:

(i) SEQUENCE CHARACTERISTICS:
  (A) LENGTH: 438 amino acids
  (B) TYPE: amino acid
  (C) STRANDEDNESS: single
  (D) TOPOLOGY: linear (ii) MOLECULE TYPE: protein (ix) FEATURE:
  (A) NAME/KEY: Protein
  (B) LOCATION: 1..438
  (D) OTHER INFORMATION: /note= "PRE-PRO-VGR1"

(x) PUBLICATION INFORMATION:
  (A) AUTHORS: LYONS,
  (C) JOURNAL: Proc. Natl. Acad. Sci. U.S.A.
  (D) VOLUME: 86
  (F) PAGES: 4554-4558
  (G) DATE: 1989

(xi) SEQUENCE DESCRIPTION: SEQ ID NO:14:

```
Met  Arg  Lys  Met  Gln  Lys  Glu  Ile  Leu  Ser  Val  Leu  Gly  Pro  Pro  His
1                   5                        10                      15

Arg  Pro  Arg  Pro  Leu  His  Gly  Leu  Gln  Gln  Pro  Gln  Pro  Pro  Val  Leu
               20                 25                      30

Pro  Pro  Gln  Gln  Gln  Gln  Gln  Gln  Gln  Gln  Gln  Gln  Thr  Ala  Asp  Glu
          35                 40                      45

Glu  Pro  Pro  Pro  Gly  Arg  Leu  Lys  Ser  Ala  Pro  Leu  Phe  Met  Leu  Asp
     50                 55                      60

Leu  Tyr  Asn  Ala  Leu  Ser  Asn  Asp  Asp  Glu  Glu  Asp  Gly  Ala  Ser  Glu
65                      70                 75                           80

Gly  Val  Gly  Gln  Glu  Pro  Gly  Ser  His  Gly  Gly  Ala  Ser  Ser  Ser  Gln
               85                 90                      95

Leu  Arg  Gln  Pro  Ser  Pro  Gly  Ala  Ala  His  Ser  Leu  Asn  Arg  Lys  Ser
               100                105                     110

Leu  Leu  Ala  Pro  Gly  Pro  Gly  Gly  Ala  Ser  Pro  Leu  Thr  Ser  Ala
               115                120                     125

Gln  Asp  Ser  Ala  Phe  Leu  Asn  Asp  Ala  Asp  Met  Val  Met  Ser  Phe  Val
```

```
                    1 3 0                           1 3 5                           1 4 0
    Asn   Leu   Val   Gly   Tyr   Asp   Lys   Glu   Phe   Ser   Pro   His   Gln   Arg   His   His
    1 4 5                           1 5 0                           1 5 5                           1 6 0

Lys   Glu   Phe   Lys   Phe   Asn   Leu   Ser   Gln   Ile   Pro   Glu   Gly   Glu   Ala   Val
                                  1 6 5                           1 7 0                           1 7 5

Thr   Ala   Ala   Glu   Phe   Arg   Val   Tyr   Lys   Asp   Cys   Val   Val   Gly   Ser   Phe
                            1 8 0                           1 8 5                           1 9 0

Lys   Asn   Gln   Thr   Phe   Leu   Ile   Ser   Ile   Tyr   Gln   Val   Leu   Gln   Glu   Ala
                      1 9 5                           2 0 0                           2 0 5

Gln   His   Arg   Asp   Ser   Asp   Leu   Phe   Leu   Leu   Asp   Thr   Arg   Val   Val   Trp
                2 1 0                           2 1 5                           2 2 0

Ala   Ser   Glu   Glu   Gly   Trp   Leu   Glu   Phe   Asp   Ile   Thr   Ala   Thr   Ser   Asn
    2 2 5                           2 3 0                           2 3 5                           2 4 0

Leu   Trp   Val   Val   Ile   Pro   Gln   His   Asn   Met   Gly   Leu   Gln   Leu   Ser   Val
                            2 4 5                           2 5 0                           2 5 5

Val   Thr   Arg   Asp   Gly   Leu   His   Val   Asn   Pro   Arg   Ala   Ala   Gly   Leu   Val
                      2 6 0                           2 6 5                           2 7 0

Gly   Arg   Asp   Gly   Pro   Tyr   Asp   Lys   Gln   Pro   Phe   Met   Val   Ala   Phe   Phe
                2 7 5                           2 8 0                           2 8 5

Lys   Val   Ser   Glu   Val   His   Val   Arg   Thr   Thr   Arg   Ser   Ala   Ser   Ser   Arg
          2 9 0                           2 9 5                           3 0 0

Arg   Arg   Gln   Gln   Ser   Arg   Asn   Arg   Ser   Thr   Gln   Ser   Gln   Asp   Val   Ser
    3 0 5                           3 1 0                           3 1 5                           3 2 0

Arg   Gly   Ser   Gly   Ser   Ser   Asp   Tyr   Asn   Gly   Ser   Glu   Leu   Lys   Thr   Ala
                            3 2 5                           3 3 0                           3 3 5

Cys   Lys   Lys   His   Glu   Leu   Tyr   Val   Ser   Phe   Gln   Asp   Leu   Gly   Trp   Gln
                      3 4 0                           3 4 5                           3 5 0

Asp   Trp   Ile   Ile   Ala   Pro   Lys   Gly   Tyr   Ala   Ala   Asn   Tyr   Cys   Asp   Gly
                3 5 5                           3 6 0                           3 6 5

Glu   Cys   Ser   Phe   Pro   Leu   Asn   Ala   His   Met   Asn   Ala   Thr   Asn   His   Ala
          3 7 0                           3 7 5                           3 8 0

Ile   Val   Gln   Thr   Leu   Val   His   Leu   Met   Asn   Pro   Glu   Thr   Val   Pro   Lys
    3 8 5                           3 9 0                           3 9 5                           4 0 0

Pro   Cys   Cys   Ala   Pro   Thr   Lys   Leu   Asn   Ala   Ile   Ser   Val   Leu   Tyr   Phe
                            4 0 5                           4 1 0                           4 1 5

Asp   Asp   Asn   Ser   Asn   Val   Ile   Leu   Lys   Lys   Tyr   Arg   Asn   Met   Val   Val
                      4 2 0                           4 2 5                           4 3 0

Arg   Ala   Cys   Gly   Cys   His
                4 3 5
```

( 2 ) INFORMATION FOR SEQ ID NO:15:

( i ) SEQUENCE CHARACTERISTICS:
        ( A ) LENGTH: 372 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..372
        ( D ) OTHER INFORMATION: /note= "PRE-PRO-GDF-1"

( x ) PUBLICATION INFORMATION:
        ( A ) AUTHORS: LEE,
        ( B ) TITLE: EXPRESSION OF GROWTH/DIFFERENTIATION FACTOR 1
        ( C ) JOURNAL: Proc. Natl. Acad. Sci. U.S.A.
        ( D ) VOLUME: 88

(F) PAGES: 4250-4254
(G) DATE: MAY-1991

(xi) SEQUENCE DESCRIPTION: SEQ ID NO:15:

| Met | Pro | Pro | Pro | Gln | Gln | Gly | Pro | Cys | Gly | His | His | Leu | Leu | Leu | Leu |
| 1 | | | | 5 | | | | | 10 | | | | | 15 | |

| Leu | Ala | Leu | Leu | Leu | Pro | Ser | Leu | Pro | Leu | Thr | Arg | Ala | Pro | Val | Pro |
| | | | 20 | | | | 25 | | | | | 30 | | | |

| Pro | Gly | Pro | Ala | Ala | Ala | Leu | Leu | Gln | Ala | Leu | Gly | Leu | Arg | Asp | Glu |
| | | 35 | | | | | 40 | | | | | 45 | | | |

| Pro | Gln | Gly | Ala | Pro | Arg | Leu | Arg | Pro | Val | Pro | Pro | Val | Met | Trp | Arg |
| | 50 | | | | | 55 | | | | | 60 | | | | |

| Leu | Phe | Arg | Arg | Arg | Asp | Pro | Gln | Glu | Thr | Arg | Ser | Gly | Ser | Arg | Arg |
| 65 | | | | | 70 | | | | | 75 | | | | | 80 |

| Thr | Ser | Pro | Gly | Val | Thr | Leu | Gln | Pro | Cys | His | Val | Glu | Glu | Leu | Gly |
| | | | | 85 | | | | | 90 | | | | | 95 | |

| Val | Ala | Gly | Asn | Ile | Val | Arg | His | Ile | Pro | Asp | Arg | Gly | Ala | Pro | Thr |
| | | | 100 | | | | 105 | | | | | 110 | | | |

| Arg | Ala | Ser | Glu | Pro | Val | Ser | Ala | Ala | Gly | His | Cys | Pro | Glu | Trp | Thr |
| | | 115 | | | | | 120 | | | | | 125 | | | |

| Val | Val | Phe | Asp | Leu | Ser | Ala | Val | Glu | Pro | Ala | Glu | Arg | Pro | Ser | Arg |
| | 130 | | | | | 135 | | | | | 140 | | | | |

| Ala | Arg | Leu | Glu | Leu | Arg | Phe | Ala | Ala | Ala | Ala | Ala | Ala | Ala | Pro | Glu |
| 145 | | | | | 150 | | | | | 155 | | | | | 160 |

| Gly | Gly | Trp | Glu | Leu | Ser | Val | Ala | Gln | Ala | Gly | Gln | Gly | Ala | Gly | Ala |
| | | | | 165 | | | | | 170 | | | | | 175 | |

| Asp | Pro | Gly | Pro | Val | Leu | Leu | Arg | Gln | Leu | Val | Pro | Ala | Leu | Gly | Pro |
| | | | 180 | | | | 185 | | | | | 190 | | | |

| Pro | Val | Arg | Ala | Glu | Leu | Leu | Gly | Ala | Ala | Trp | Ala | Arg | Asn | Ala | Ser |
| | | 195 | | | | | 200 | | | | | 205 | | | |

| Trp | Pro | Arg | Ser | Leu | Arg | Leu | Ala | Leu | Ala | Leu | Arg | Pro | Arg | Ala | Pro |
| | 210 | | | | | 215 | | | | | 220 | | | | |

| Ala | Ala | Cys | Ala | Arg | Leu | Ala | Glu | Ala | Ser | Leu | Leu | Leu | Val | Thr | Leu |
| 225 | | | | | 230 | | | | | 235 | | | | | 240 |

| Asp | Pro | Arg | Leu | Cys | His | Pro | Leu | Ala | Arg | Pro | Arg | Arg | Asp | Ala | Glu |
| | | | | 245 | | | | | 250 | | | | | 255 | |

| Pro | Val | Leu | Gly | Gly | Gly | Pro | Gly | Gly | Ala | Cys | Arg | Ala | Arg | Arg | Leu |
| | | | 260 | | | | 265 | | | | | 270 | | | |

| Tyr | Val | Ser | Phe | Arg | Glu | Val | Gly | Trp | His | Arg | Trp | Val | Ile | Ala | Pro |
| | | 275 | | | | | 280 | | | | | 285 | | | |

| Arg | Gly | Phe | Leu | Ala | Asn | Tyr | Cys | Gln | Gly | Gln | Cys | Ala | Leu | Pro | Val |
| | 290 | | | | | 295 | | | | | 300 | | | | |

| Ala | Leu | Ser | Gly | Ser | Gly | Gly | Pro | Pro | Ala | Leu | Asn | His | Ala | Val | Leu |
| 305 | | | | | 310 | | | | | 315 | | | | | 320 |

| Arg | Ala | Leu | Met | His | Ala | Ala | Ala | Pro | Gly | Ala | Ala | Asp | Leu | Pro | Cys |
| | | | | 325 | | | | | 330 | | | | | 335 | |

| Cys | Val | Pro | Ala | Arg | Leu | Ser | Pro | Ile | Ser | Val | Leu | Phe | Phe | Asp | Asn |
| | | | 340 | | | | 345 | | | | | 350 | | | |

| Ser | Asp | Asn | Val | Val | Leu | Arg | Gln | Tyr | Glu | Asp | Met | Val | Val | Asp | Glu |
| | | 355 | | | | | 360 | | | | | 365 | | | |

| Cys | Gly | Cys | Arg |
| | 370 | | |

(2) INFORMATION FOR SEQ ID NO:16:

(i) SEQUENCE CHARACTERISTICS:
    (A) LENGTH: 455 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Protein
    (B) LOCATION: 1..455
    (D) OTHER INFORMATION: /note= "PRE-PRO 60A"

(x) PUBLICATION INFORMATION:
    (A) AUTHORS: WHARTON,
    (C) JOURNAL: Proc. Natl. Acad. Sci. U.S.A.
    (D) VOLUME: 88
    (F) PAGES: 9214-9218
    (G) DATE: 1991

(xi) SEQUENCE DESCRIPTION: SEQ ID NO:16:

```
Met Ser Gly Leu Arg Asn Thr Ser Glu Ala Val Ala Val Leu Ala Ser
1               5                   10                  15
Leu Gly Leu Gly Met Val Leu Leu Met Phe Val Ala Thr Thr Pro Pro
            20                  25                  30
Ala Val Glu Ala Thr Gln Ser Gly Ile Tyr Ile Asp Asn Gly Lys Asp
        35                  40                  45
Gln Thr Ile Met His Arg Val Leu Ser Glu Asp Lys Leu Asp Val
    50                  55                  60
Ser Tyr Glu Ile Leu Glu Phe Leu Gly Ile Ala Glu Arg Pro Thr His
65                  70                  75                  80
Leu Ser Ser His Gln Leu Ser Leu Arg Lys Ser Ala Pro Lys Phe Leu
                85                  90                  95
Leu Asp Val Tyr His Arg Ile Thr Ala Glu Glu Gly Leu Ser Asp Gln
            100                 105                 110
Asp Glu Asp Asp Asp Tyr Glu Arg Gly His Arg Ser Arg Arg Ser Ala
            115                 120                 125
Asp Leu Glu Glu Asp Glu Gly Glu Gln Gln Lys Asn Phe Ile Thr Asp
            130                 135                 140
Leu Asp Lys Arg Ala Ile Asp Glu Ser Asp Ile Ile Met Thr Phe Leu
145                 150                 155                 160
Asn Lys Arg His His Asn Val Asp Glu Leu Arg His Glu His Gly Arg
                165                 170                 175
Arg Leu Trp Phe Asp Val Ser Asn Val Pro Asn Asp Asn Tyr Leu Val
            180                 185                 190
Met Ala Glu Leu Arg Ile Tyr Gln Asn Ala Asn Glu Gly Lys Trp Leu
            195                 200                 205
Thr Ala Asn Arg Glu Phe Thr Ile Thr Val Tyr Ala Ile Gly Thr Gly
210                 215                 220
Thr Leu Gly Gln His Thr Met Glu Pro Leu Ser Ser Val Asn Thr Thr
225                 230                 235                 240
Gly Asp Tyr Val Gly Trp Leu Glu Leu Asn Val Thr Glu Gly Leu His
            245                 250                 255
Glu Trp Leu Val Lys Ser Lys Asp Asn His Gly Ile Tyr Ile Gly Ala
            260                 265                 270
His Ala Val Asn Arg Pro Asp Arg Glu Val Lys Leu Asp Ile Gly
        275                 280                 285
Leu Ile His Arg Lys Val Asp Asp Glu Phe Gln Pro Phe Met Ile Gly
        290                 295                 300
Phe Phe Arg Gly Pro Glu Leu Ile Lys Ala Thr Ala His Ser Ser His
```

|  |  |  |  | 305 |  |  |  | 310 |  |  |  | 315 |  |  | 320 |
|---|---|---|---|---|---|---|---|---|---|---|---|---|---|---|---|
| His | Arg | Ser | Lys | Arg 325 | Ser | Ala | Ser | His | Pro 330 | Arg | Lys | Arg | Lys 335 | Lys | Ser |
| Val | Ser | Pro | Asn 340 | Asn | Val | Pro | Leu | Leu 345 | Glu | Pro | Met | Glu | Ser 350 | Thr | Arg |
| Ser | Cys | Gln 355 | Met | Gln | Thr | Leu | Tyr 360 | Ile | Asp | Phe | Lys | Asp 365 | Leu | Gly | Trp |
| His | Asp 370 | Trp | Ile | Ile | Ala | Pro 375 | Glu | Gly | Tyr | Gly | Ala 380 | Phe | Tyr | Cys | Ser |
| Gly 385 | Glu | Cys | Asn | Phe | Pro 390 | Leu | Asn | Ala | His | Met 395 | Asn | Ala | Thr | Asn | His 400 |
| Ala | Ile | Val | Gln | Thr 405 | Leu | Val | His | Leu | Leu 410 | Glu | Pro | Lys | Lys | Val 415 | Pro |
| Lys | Pro | Cys | Cys 420 | Ala | Pro | Thr | Arg | Leu 425 | Gly | Ala | Leu | Pro | Val 430 | Leu | Tyr |
| His | Leu | Asn 435 | Asp | Glu | Asn | Val | Asn 440 | Leu | Lys | Lys | Tyr | Arg 445 | Asn | Met | Ile |
| Val | Lys 450 | Ser | Cys | Gly | Cys | His 455 |  |  |  |  |  |  |  |  |  |

( 2 ) INFORMATION FOR SEQ ID NO:17:

( i ) SEQUENCE CHARACTERISTICS:
( A ) LENGTH: 472 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..472
( D ) OTHER INFORMATION: /note= "PRE-PRO-BMP3"

( x ) PUBLICATION INFORMATION:
( A ) AUTHORS: WOZNEY,
( C ) JOURNAL: SCIENCE
( D ) VOLUME: 242
( F ) PAGES: 1528-1534
( G ) DATE: 1988

( x i ) SEQUENCE DESCRIPTION: SEQ ID NO:17:

| Met 1 | Ala | Gly | Ala | Ser 5 | Arg | Leu | Leu | Phe | Leu 10 | Trp | Leu | Gly | Cys | Phe 15 | Cys |
|---|---|---|---|---|---|---|---|---|---|---|---|---|---|---|---|
| Val | Ser | Leu | Ala 20 | Gln | Gly | Glu | Arg | Pro 25 | Lys | Pro | Pro | Phe | Pro 30 | Glu | Leu |
| Arg | Lys | Ala 35 | Val | Pro | Gly | Asp | Arg 40 | Thr | Ala | Gly | Gly | Gly 45 | Pro | Asp | Ser |
| Glu | Leu 50 | Gln | Pro | Gln | Asp | Lys 55 | Val | Ser | Glu | His | Met 60 | Leu | Arg | Leu | Tyr |
| Asp 65 | Arg | Tyr | Ser | Thr | Val 70 | Gln | Ala | Ala | Arg | Thr 75 | Pro | Gly | Ser | Leu | Glu 80 |
| Gly | Gly | Ser | Gln | Pro 85 | Trp | Arg | Pro | Arg | Leu 90 | Leu | Arg | Glu | Gly | Asn 95 | Thr |
| Val | Arg | Ser | Phe 100 | Arg | Ala | Ala | Ala | Ala 105 | Glu | Thr | Leu | Glu | Arg 110 | Lys | Gly |
| Leu | Tyr | Ile 115 | Phe | Asn | Leu | Thr | Ser 120 | Leu | Thr | Lys | Ser | Glu 125 | Asn | Ile | Leu |
| Ser | Ala 130 | Thr | Leu | Tyr | Phe | Cys 135 | Ile | Gly | Glu | Leu | Gly 140 | Asn | Ile | Ser | Leu |

| | | | | | | | | | | | | | | | |
|---|---|---|---|---|---|---|---|---|---|---|---|---|---|---|---|
| Ser | Cys | Pro | Val | Ser | Gly | Gly | Cys | Ser | His | His | Ala | Gln | Arg | Lys | His |
| 145 | | | | 150 | | | | | 155 | | | | | | 160 |
| Ile | Gln | Ile | Asp | Leu | Ser | Ala | Trp | Thr | Leu | Lys | Phe | Ser | Arg | Asn | Gln |
| | | | | 165 | | | | | 170 | | | | | 175 | |
| Ser | Gln | Leu | Leu | Gly | His | Leu | Ser | Val | Asp | Met | Ala | Lys | Ser | His | Arg |
| | | | 180 | | | | | 185 | | | | | 190 | | |
| Asp | Ile | Met | Ser | Trp | Leu | Ser | Lys | Asp | Ile | Thr | Gln | Phe | Leu | Arg | Lys |
| | | | 195 | | | | 200 | | | | | 205 | | | |
| Ala | Lys | Glu | Asn | Glu | Phe | Leu | Ile | Gly | Phe | Asn | Ile | Thr | Ser | Lys |
| | 210 | | | | | 215 | | | | | 220 | | | | |
| Gly | Arg | Gln | Leu | Pro | Lys | Arg | Arg | Leu | Pro | Phe | Pro | Glu | Pro | Tyr | Ile |
| 225 | | | | | 230 | | | | | 235 | | | | | 240 |
| Leu | Val | Tyr | Ala | Asn | Asp | Ala | Ala | Ile | Ser | Glu | Pro | Glu | Ser | Val | Val |
| | | | | 245 | | | | | 250 | | | | | 255 | |
| Ser | Ser | Leu | Gln | Gly | His | Arg | Asn | Phe | Pro | Thr | Gly | Thr | Val | Pro | Lys |
| | | | 260 | | | | | 265 | | | | | 270 | | |
| Trp | Asp | Ser | His | Ile | Arg | Ala | Ala | Leu | Ser | Ile | Glu | Arg | Arg | Lys | Lys |
| | | | 275 | | | | 280 | | | | | 285 | | | |
| Arg | Ser | Thr | Gly | Val | Leu | Leu | Pro | Leu | Gln | Asn | Asn | Glu | Leu | Pro | Gly |
| | 290 | | | | | 295 | | | | | 300 | | | | |
| Ala | Glu | Tyr | Gln | Tyr | Lys | Lys | Asp | Glu | Val | Trp | Glu | Glu | Arg | Lys | Pro |
| 305 | | | | | 310 | | | | | 315 | | | | | 320 |
| Tyr | Lys | Thr | Leu | Gln | Ala | Gln | Ala | Pro | Glu | Lys | Ser | Lys | Asn | Lys | Lys |
| | | | | 325 | | | | | 330 | | | | | 335 | |
| Lys | Gln | Arg | Lys | Gly | Pro | His | Arg | Lys | Ser | Gln | Thr | Leu | Gln | Phe | Asp |
| | | | 340 | | | | | 345 | | | | | 350 | | |
| Glu | Gln | Thr | Leu | Lys | Lys | Ala | Arg | Arg | Lys | Gln | Trp | Ile | Glu | Pro | Arg |
| | | | 355 | | | | 360 | | | | | 365 | | | |
| Asn | Cys | Ala | Arg | Arg | Tyr | Leu | Lys | Val | Asp | Phe | Ala | Asp | Ile | Gly | Trp |
| | 370 | | | | | 375 | | | | | 380 | | | | |
| Ser | Glu | Trp | Ile | Ile | Ser | Pro | Lys | Ser | Phe | Asp | Ala | Tyr | Tyr | Cys | Ser |
| 385 | | | | | 390 | | | | | 395 | | | | | 400 |
| Gly | Ala | Cys | Gln | Phe | Pro | Met | Pro | Lys | Ser | Leu | Lys | Pro | Ser | Asn | His |
| | | | | 405 | | | | | 410 | | | | | 415 | |
| Ala | Thr | Ile | Gln | Ser | Ile | Val | Arg | Ala | Val | Gly | Val | Val | Pro | Gly | Ile |
| | | | 420 | | | | | 425 | | | | | 430 | | |
| Pro | Glu | Pro | Cys | Cys | Val | Pro | Glu | Lys | Met | Ser | Ser | Leu | Ser | Ile | Leu |
| | | | 435 | | | | | 440 | | | | | 445 | | |
| Phe | Phe | Asp | Glu | Asn | Lys | Asn | Val | Val | Leu | Lys | Val | Tyr | Pro | Asn | Met |
| | | 450 | | | | | 455 | | | | | 460 | | | |
| Thr | Val | Glu | Ser | Cys | Ala | Cys | Arg |
| 465 | | | | | 470 | | |

( 2 ) INFORMATION FOR SEQ ID NO:18:

( i ) SEQUENCE CHARACTERISTICS:
        ( A ) LENGTH: 453 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..453
        ( D ) OTHER INFORMATION: /note= "PRE-PRO-BMP5 (HUMAN)"

( x ) PUBLICATION INFORMATION:
  ( A ) AUTHORS: CELESTE,
  ( C ) JOURNAL: Proc. Natl. Acad. Sci. U.S.A.
  ( D ) VOLUME: 87
  ( F ) PAGES: 9843-9847
  ( G ) DATE: 1991

( x i ) SEQUENCE DESCRIPTION: SEQ ID NO:18:

```
Met  His  Leu  Thr  Val  Phe  Leu  Leu  Lys  Gly  Ile  Val  Gly  Phe  Leu  Trp
1              5                        10                       15

Ser  Cys  Trp  Val  Leu  Val  Gly  Tyr  Ala  Lys  Gly  Gly  Leu  Gly  Asp  Asn
              20                       25                      30

His  Val  His  Ser  Ser  Phe  Ile  Tyr  Arg  Arg  Leu  Arg  Asn  His  Glu  Arg
              35                       40                      45

Arg  Glu  Ile  Gln  Arg  Glu  Ile  Leu  Ser  Ile  Leu  Gly  Leu  Pro  His  Arg
         50                       55                      60

Pro  Arg  Pro  Phe  Ser  Pro  Gly  Lys  Gln  Ala  Ser  Ser  Ala  Pro  Leu  Phe
65                       70                      75                       80

Met  Leu  Asp  Leu  Tyr  Asn  Ala  Met  Thr  Asn  Glu  Glu  Asn  Pro  Glu  Glu
              85                       90                      95

Ser  Glu  Tyr  Ser  Val  Arg  Ala  Ser  Leu  Ala  Glu  Glu  Thr  Arg  Gly  Ala
              100                      105                     110

Arg  Lys  Gly  Tyr  Pro  Ala  Ser  Pro  Asn  Gly  Tyr  Pro  Arg  Arg  Ile  Gln
              115                      120                     125

Leu  Ser  Arg  Thr  Thr  Pro  Leu  Thr  Thr  Gln  Ser  Pro  Pro  Leu  Ala  Ser
              130                      135                     140

Leu  His  Asp  Thr  Asn  Phe  Leu  Asn  Asp  Ala  Asp  Met  Val  Met  Ser  Phe
145                      150                      155                      160

Val  Asn  Leu  Val  Glu  Arg  Asp  Lys  Asp  Phe  Ser  His  Gln  Arg  Arg  His
                    165                      170                     175

Tyr  Lys  Glu  Arg  Phe  Asp  Leu  Thr  Gln  Ile  Pro  His  Gly  Glu  Ala  Val
              180                      185                     190

Thr  Ala  Ala  Glu  Phe  Arg  Ile  Tyr  Lys  Asp  Arg  Ser  Asn  Asn  Arg  Phe
         195                      200                      205

Glu  Asn  Glu  Thr  Ile  Lys  Ile  Ser  Ile  Tyr  Gln  Ile  Ile  Lys  Glu  Tyr
     210                      215                      220

Thr  Asn  Arg  Asp  Ala  Asp  Leu  Phe  Leu  Leu  Asp  Thr  Arg  Lys  Ala  Gln
225                      230                      235                      240

Ala  Leu  Asp  Val  Gly  Trp  Leu  Val  Phe  Asp  Ile  Thr  Val  Thr  Ser  Asn
                    245                      250                     255

His  Trp  Val  Ile  Asn  Pro  Gln  Asn  Asn  Leu  Gly  Leu  Gln  Leu  Cys  Ala
                    260                      265                     270

Glu  Thr  Gly  Asp  Gly  Arg  Ser  Ile  Asn  Val  Lys  Ser  Ala  Gly  Leu  Val
              275                      280                     285

Gly  Arg  Gln  Gly  Pro  Gln  Ser  Lys  Gln  Pro  Phe  Met  Val  Ala  Phe  Phe
     290                      295                      300

Lys  Ala  Ser  Glu  Val  Leu  Leu  Arg  Ser  Val  Arg  Ala  Ala  Asn  Lys  Arg
305                      310                      315                      320

Lys  Asn  Gln  Asn  Arg  Asn  Lys  Ser  Ser  Ser  His  Gln  Asp  Ser  Ser  Arg
                    325                      330                     335

Met  Ser  Ser  Val  Gly  Asp  Tyr  Asn  Thr  Ser  Glu  Gln  Lys  Gln  Ala  Cys
              340                      345                     350

Lys  Lys  His  Glu  Leu  Tyr  Val  Ser  Phe  Arg  Asp  Leu  Gly  Trp  Gln  Asp
              355                      360                     365

Trp  Ile  Ile  Ala  Pro  Glu  Gly  Tyr  Ala  Ala  Phe  Tyr  Cys  Asp  Gly  Glu
              370                      375                     380
```

```
Cys  Ser  Phe  Pro  Leu  Asn  Ala  His  Met  Asn  Ala  Thr  Asn  His  Ala  Ile
385                 390                      395                           400

Val  Gln  Thr  Leu  Val  His  Leu  Met  Phe  Pro  Asp  His  Val  Pro  Lys  Pro
                    405                      410                      415

Cys  Cys  Ala  Pro  Thr  Lys  Leu  Asn  Ala  Ile  Ser  Val  Leu  Tyr  Phe  Asp
                420                      425                      430

Asp  Ser  Ser  Asn  Val  Ile  Leu  Lys  Lys  Tyr  Arg  Asn  Met  Val  Val  Arg
          435                      440                      445

Ser  Cys  Gly  Cys  His
450
```

( 2 ) INFORMATION FOR SEQ ID NO:19:

( i ) SEQUENCE CHARACTERISTICS:
      ( A ) LENGTH: 513 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..513
      ( D ) OTHER INFORMATION: /note= "PRE-PRO-BMP6 (HUMAN)"

( x ) PUBLICATION INFORMATION:
      ( A ) AUTHORS: CELESTE,
      ( C ) JOURNAL: Proc. Natl. Acad. Sci. U.S.A.
      ( D ) VOLUME: 87
      ( F ) PAGES: 9843-9847
      ( G ) DATE: 1991

( x i ) SEQUENCE DESCRIPTION: SEQ ID NO:19:

```
Met  Pro  Gly  Leu  Gly  Arg  Arg  Ala  Gln  Trp  Leu  Cys  Trp  Trp  Trp  Gly
1                   5                        10                          15

Leu  Leu  Cys  Ser  Cys  Cys  Gly  Pro  Pro  Leu  Arg  Pro  Pro  Leu  Pro
               20                 25                      30

Ala  Ala  Ala  Ala  Ala  Ala  Ala  Gly  Gly  Gln  Leu  Leu  Gly  Asp  Gly  Gly
               35                 40                      45

Ser  Pro  Gly  Arg  Thr  Glu  Gln  Pro  Pro  Pro  Ser  Pro  Gln  Ser  Ser  Ser
     50                      55                      60

Gly  Phe  Leu  Tyr  Arg  Arg  Leu  Lys  Thr  Gln  Glu  Lys  Arg  Glu  Met  Gln
65                       70                 75                          80

Lys  Glu  Ile  Leu  Ser  Val  Leu  Gly  Leu  Pro  His  Arg  Pro  Arg  Pro  Leu
               85                      90                      95

His  Gly  Leu  Gln  Gln  Pro  Gln  Pro  Pro  Ala  Leu  Arg  Gln  Gln  Glu  Glu
               100                     105                     110

Gln  Gln  Gln  Gln  Gln  Gln  Leu  Pro  Arg  Gly  Glu  Pro  Pro  Pro  Gly  Arg
               115                     120                     125

Leu  Lys  Ser  Ala  Pro  Leu  Phe  Met  Leu  Asp  Leu  Tyr  Asn  Ala  Leu  Ser
     130                     135                     140

Ala  Asp  Asn  Asp  Glu  Asp  Gly  Ala  Ser  Glu  Gly  Glu  Arg  Gln  Gln  Ser
145                     150                     155                     160

Trp  Pro  His  Glu  Ala  Ala  Ser  Ser  Ser  Gln  Arg  Arg  Gln  Pro  Pro  Pro
                    165                     170                     175

Gly  Ala  Ala  His  Pro  Leu  Asn  Arg  Lys  Ser  Leu  Leu  Ala  Pro  Gly  Ser
                180                     185                     190

Gly  Ser  Gly  Gly  Ala  Ser  Pro  Leu  Thr  Ser  Ala  Gln  Asp  Ser  Ala  Phe
          195                     200                     205
```

| | | | | | | | | | | | | | |
|---|---|---|---|---|---|---|---|---|---|---|---|---|---|
| Leu | Asn | Asp | Ala | Asp | Met | Val | Met | Ser | Phe | Val | Asn | Leu | Val | Glu | Tyr |
| | 210 | | | | 215 | | | | | 220 | | | | | |
| Asp | Lys | Glu | Phe | Ser | Pro | Arg | Gln | Arg | His | His | Lys | Glu | Phe | Lys | Phe |
| 225 | | | | | 230 | | | | | 235 | | | | | 240 |
| Asn | Leu | Ser | Gln | Ile | Pro | Glu | Gly | Glu | Val | Val | Thr | Ala | Ala | Glu | Phe |
| | | | | 245 | | | | | 250 | | | | | 255 | |
| Arg | Ile | Tyr | Lys | Asp | Cys | Val | Met | Gly | Ser | Phe | Lys | Asn | Gln | Thr | Phe |
| | | | 260 | | | | | 265 | | | | | 270 | | |
| Leu | Ile | Ser | Ile | Tyr | Gln | Val | Leu | Gln | Glu | His | Gln | His | Arg | Asp | Ser |
| | | 275 | | | | | 280 | | | | | 285 | | | |
| Asp | Leu | Phe | Leu | Leu | Asp | Thr | Arg | Val | Val | Trp | Ala | Ser | Glu | Glu | Gly |
| | 290 | | | | | 295 | | | | | 300 | | | | |
| Trp | Leu | Glu | Phe | Asp | Ile | Thr | Ala | Thr | Ser | Asn | Leu | Trp | Val | Val | Thr |
| 305 | | | | | 310 | | | | | 315 | | | | | 320 |
| Pro | Gln | His | Asn | Met | Gly | Leu | Gln | Leu | Ser | Val | Val | Thr | Arg | Asp | Gly |
| | | | | 325 | | | | | 330 | | | | | 335 | |
| Val | His | Val | His | Pro | Arg | Ala | Ala | Gly | Leu | Val | Gly | Arg | Asp | Gly | Pro |
| | | | 340 | | | | | 345 | | | | | 350 | | |
| Tyr | Asp | Lys | Gln | Pro | Phe | Met | Val | Ala | Phe | Phe | Lys | Val | Ser | Glu | Val |
| | | 355 | | | | | 360 | | | | | 365 | | | |
| His | Val | Arg | Thr | Thr | Arg | Ser | Ala | Ser | Ser | Arg | Arg | Arg | Gln | Gln | Ser |
| | 370 | | | | | 375 | | | | | 380 | | | | |
| Arg | Asn | Arg | Ser | Thr | Gln | Ser | Gln | Asp | Val | Ala | Arg | Val | Ser | Ser | Ala |
| 385 | | | | | 390 | | | | | 395 | | | | | 400 |
| Ser | Asp | Tyr | Asn | Ser | Ser | Glu | Leu | Lys | Thr | Ala | Cys | Arg | Lys | His | Glu |
| | | | | 405 | | | | | 410 | | | | | 415 | |
| Leu | Tyr | Val | Ser | Phe | Gln | Asp | Leu | Gly | Trp | Gln | Asp | Trp | Ile | Ile | Ala |
| | | | 420 | | | | | 425 | | | | | 430 | | |
| Pro | Lys | Gly | Tyr | Ala | Ala | Asn | Tyr | Cys | Asp | Gly | Glu | Cys | Ser | Phe | Pro |
| | | 435 | | | | | 440 | | | | | 445 | | | |
| Leu | Asn | Ala | His | Met | Asn | Ala | Thr | Asn | His | Ala | Ile | Val | Gln | Thr | Leu |
| | 450 | | | | | 455 | | | | | 460 | | | | |
| Val | His | Leu | Met | Asn | Pro | Glu | Tyr | Val | Pro | Lys | Pro | Cys | Cys | Ala | Pro |
| 465 | | | | | 470 | | | | | 475 | | | | | 480 |
| Thr | Lys | Leu | Asn | Ala | Ile | Ser | Val | Leu | Tyr | Phe | Asp | Asp | Asn | Ser | Asn |
| | | | | 485 | | | | | 490 | | | | | 495 | |
| Val | Ile | Leu | Lys | Lys | Tyr | Arg | Asn | Met | Val | Val | Arg | Ala | Cys | Gly | Cys |
| | | | 500 | | | | | 505 | | | | | 510 | | |
| His | | | | | | | | | | | | | | | |

( 2 ) INFORMATION FOR SEQ ID NO:20:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=Generic-Seq-7
           / note= "wherein each Xaa is independently selected
           from a group of one or more specified amino acids
           as defined in the specification."

( x i ) SEQUENCE DESCRIPTION: SEQ ID NO:20:

| Leu | Xaa | Xaa | Xaa | Phe | Xaa | Xaa | Xaa | Gly | Trp | Xaa | Xaa | Xaa | Xaa | Xaa | Xaa |
| 1 | | | | 5 | | | | | 10 | | | | | 15 | |
| Pro | Xaa | Xaa | Xaa | Xaa | Ala | Xaa | Tyr | Cys | Xaa | Gly | Xaa | Cys | Xaa | Xaa | Pro |
| | | | 20 | | | | | 25 | | | | | 30 | | |
| Xaa | Xaa | Xaa | Xaa | Xaa | Xaa | Xaa | Xaa | Asn | His | Ala | Xaa | Xaa | Xaa | Xaa | Xaa |
| | | | 35 | | | | | 40 | | | | | 45 | | |
| Xaa | Xaa | Xaa | Xaa | Xaa | Xaa | Xaa | Xaa | Xaa | Xaa | Xaa | Xaa | Cys | Cys | Xaa | Pro |
| | | 50 | | | | | | 55 | | | | | 60 | | |
| Xaa | Xaa | Xaa | Xaa | Xaa | Xaa | Xaa | Xaa | Leu | Xaa | Xaa | Xaa | Xaa | Xaa | Xaa | Xaa |
| 65 | | | | | | 70 | | | | | 75 | | | | 80 |
| Val | Xaa | Leu | Xaa | Xaa | Xaa | Xaa | Xaa | Met | Xaa | Val | Xaa | Xaa | Cys | Xaa | Cys |
| | | | | 85 | | | | | 90 | | | | | 95 | |
| Xaa | | | | | | | | | | | | | | | |

(2) INFORMATION FOR SEQ ID NO:21:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=Generic-Seq-8
            / note= "wherin each Xaa is independently selected from a group of one or more specified amino acids as defined in the specification."

(xi) SEQUENCE DESCRIPTION: SEQ ID NO:21:

| Cys | Xaa | Xaa | Xaa | Xaa | Leu | Xaa | Xaa | Xaa | Phe | Xaa | Xaa | Xaa | Gly | Trp | Xaa |
| 1 | | | | 5 | | | | | 10 | | | | | 15 | |
| Xaa | Xaa | Xaa | Xaa | Xaa | Pro | Xaa | Xaa | Xaa | Xaa | Ala | Xaa | Tyr | Cys | Xaa | Gly |
| | | | 20 | | | | | 25 | | | | | 30 | | |
| Xaa | Cys | Xaa | Xaa | Pro | Xaa | Xaa | Xaa | Xaa | Xaa | Xaa | Xaa | Xaa | Asn | His | Ala |
| | | | 35 | | | | | 40 | | | | | 45 | | |
| Xaa | Xaa | Xaa | Xaa | Xaa | Xaa | Xaa | Xaa | Xaa | Xaa | Xaa | Xaa | Xaa | Xaa | Xaa | Xaa |
| | | 50 | | | | | | 55 | | | | | 60 | | |
| Xaa | Cys | Cys | Xaa | Pro | Xaa | Xaa | Xaa | Xaa | Xaa | Xaa | Xaa | Xaa | Leu | Xaa | Xaa |
| 65 | | | | | | 70 | | | | | 75 | | | | 80 |
| Xaa | Xaa | Xaa | Xaa | Xaa | Val | Xaa | Leu | Xaa | Xaa | Xaa | Xaa | Xaa | Met | Xaa | Val |
| | | | | 85 | | | | | 90 | | | | | 95 | |
| Xaa | Xaa | Cys | Xaa | Cys | Xaa | | | | | | | | | | |
| | | | 100 | | | | | | | | | | | | |

(2) INFORMATION FOR SEQ ID NO:22:

(i) SEQUENCE CHARACTERISTICS:
        (A) LENGTH: 102 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=OPX
            / note= "WHEREIN EACH XAA IS INDEPENDENTLY SELECTED FROM A GROUP OF ONE OR MORE SPECIFIED AMINO ACIDS AS DEFINED IN THE SPECIFICATION (SECTION II.B.2.)"

(x i) SEQUENCE DESCRIPTION: SEQ ID NO:22:

| Cys | Xaa | Xaa | His | Glu | Leu | Tyr | Val | Xaa | Phe | Xaa | Asp | Leu | Gly | Trp | Xaa |
|---|---|---|---|---|---|---|---|---|---|---|---|---|---|---|---|
| 1 | | | | 5 | | | | | 10 | | | | | 15 | |
| Asp | Trp | Xaa | Ile | Ala | Pro | Xaa | Gly | Tyr | Xaa | Ala | Tyr | Tyr | Cys | Glu | Gly |
| | | | 20 | | | | | 25 | | | | | 30 | | |
| Glu | Cys | Xaa | Phe | Pro | Leu | Xaa | Ser | Xaa | Met | Asn | Ala | Thr | Asn | His | Ala |
| | | 35 | | | | | 40 | | | | | 45 | | | |
| Ile | Xaa | Gln | Xaa | Leu | Val | His | Xaa | Xaa | Xaa | Pro | Xaa | Xaa | Val | Pro | Lys |
| | 50 | | | | | 55 | | | | | 60 | | | | |
| Xaa | Cys | Cys | Ala | Pro | Thr | Xaa | Leu | Xaa | Ala | Xaa | Ser | Val | Leu | Tyr | Xaa |
| 65 | | | | | 70 | | | | | 75 | | | | | 80 |
| Asp | Xaa | Ser | Xaa | Asn | Val | Xaa | Leu | Xaa | Lys | Xaa | Arg | Asn | Met | Val | Val |
| | | | | 85 | | | | | 90 | | | | | 95 | |
| Xaa | Ala | Cys | Gly | Cys | His | | | | | | | | | | |
| | | | 100 | | | | | | | | | | | | |

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Cleavage-site
        (B) LOCATION: 1..4
        (D) OTHER INFORMATION: /note= "PROTEOLYTIC CLEAVAGE SITE"

(x i) SEQUENCE DESCRIPTION: SEQ ID NO:23:

Arg Xaa Xaa Arg
1